(12) United States Patent
Contreras-Vidal et al.

(10) Patent No.: US 10,092,205 B2
(45) Date of Patent: Oct. 9, 2018

(54) METHODS FOR CLOSED-LOOP NEURAL-MACHINE INTERFACE SYSTEMS FOR THE CONTROL OF WEARABLE EXOSKELETONS AND PROSTHETIC DEVICES

(71) Applicants: Jose L. Contreras-Vidal, Houston, TX (US); Saurabh Prasad, Houston, TX (US); Atilla Kilicarslan, Houston, TX (US); Nikunj Bhagat, Houston, TX (US)

(72) Inventors: Jose L. Contreras-Vidal, Houston, TX (US); Saurabh Prasad, Houston, TX (US); Atilla Kilicarslan, Houston, TX (US); Nikunj Bhagat, Houston, TX (US)

(73) Assignee: UNIVERSITY OF HOUSTON SYSTEM, Houston, TX (US)

( * ) Notice: Subject to any disclaimer, the term of this patent is extended or adjusted under 35 U.S.C. 154(b) by 1122 days.

(21) Appl. No.: 14/323,320

(22) Filed: Jul. 3, 2014

(65) Prior Publication Data

US 2015/0012111 A1    Jan. 8, 2015

Related U.S. Application Data

(60) Provisional application No. 61/842,673, filed on Jul. 3, 2013.

(51) Int. Cl.
*A61B 5/04*  (2006.01)
*A61B 5/0476*  (2006.01)
*A61B 5/00*  (2006.01)

(52) U.S. Cl.
CPC .......... *A61B 5/0476* (2013.01); *A61B 5/4851* (2013.01)

(58) Field of Classification Search
USPC ......................................................... 600/545
See application file for complete search history.

(56) References Cited

U.S. PATENT DOCUMENTS

| | | | |
|---|---|---|---|
| 7,209,788 | B2 | 4/2007 | Nicolelis et al. |
| 2006/0167371 | A1* | 7/2006 | Flaherty ................... A61F 2/50 600/545 |

(Continued)

FOREIGN PATENT DOCUMENTS

| | | | |
|---|---|---|---|
| WO | WO-2008151291 A1 | 3/2010 | |
| WO | WO 2011140303 A1 * | 11/2011 | ......... A61B 5/04842 |

(Continued)

OTHER PUBLICATIONS

Sugiyama, Masashi. Local Fisher Discriminant Analysis for Supervised Dimensionality Reduction. Proceedings of the 23rd International Conference on Machine Learning, pp. 905-912; Jun. 25-29, 2006.*

(Continued)

*Primary Examiner* — Etsub Berhanu
(74) *Attorney, Agent, or Firm* — Winstead PC

(57) ABSTRACT

Brain-Machine Interface (BMI) systems or movement-assist systems may be utilized to aid users with paraplegia or tetraplegia in ambulation or other movement or in rehabilitation of motor function after brain injury or neurological disease, such as stroke, Parkinson's disease or cerebral palsy. The BMI may translate one or more neural signals into a movement type, a discrete movement or gesture or a series of movements, performed by an actuator. System and methods of decoding a locomotion-impaired and/or an upper-arm impaired subject's intent with the BMI may utilize non-invasive methods to provide the subject the ability to make the desired motion using an actuator or command a virtual avatar.

18 Claims, 19 Drawing Sheets

(56) References Cited

U.S. PATENT DOCUMENTS

| | | |
|---|---|---|
| 2006/0189901 A1 | 8/2006 | Flaherty et al. |
| 2006/0206167 A1 | 9/2006 | Flaherty et al. |
| 2011/0028827 A1* | 2/2011 | Sitaram ................ A61B 5/0059 600/410 |
| 2012/0071780 A1* | 3/2012 | Barachant .......... A61B 5/04012 600/544 |
| 2012/0101401 A1* | 4/2012 | Faul .................... A61B 5/0476 600/544 |
| 2014/0058528 A1 | 2/2014 | Contreras-Vidal et al. |

FOREIGN PATENT DOCUMENTS

| | | |
|---|---|---|
| WO | WO-2011140303 A1 | 11/2011 |
| WO | WO-2003037231 A1 | 8/2012 |

OTHER PUBLICATIONS

Li et al. Locality-Preserving Dimensionality Reduction and Classification for Hyperspectral Image Analysis. IEEE Transactions on Geoscience and Remote Sensing, vol. 50, No. 4, Apr. 2012.*

* cited by examiner

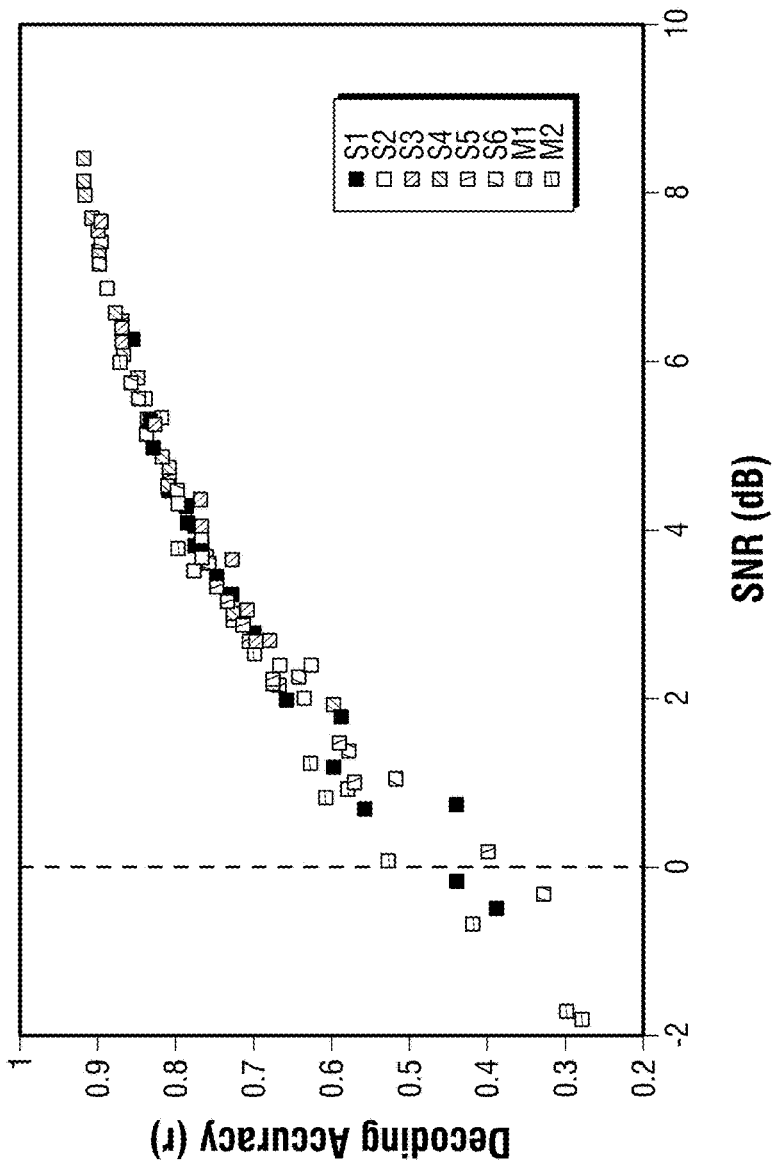
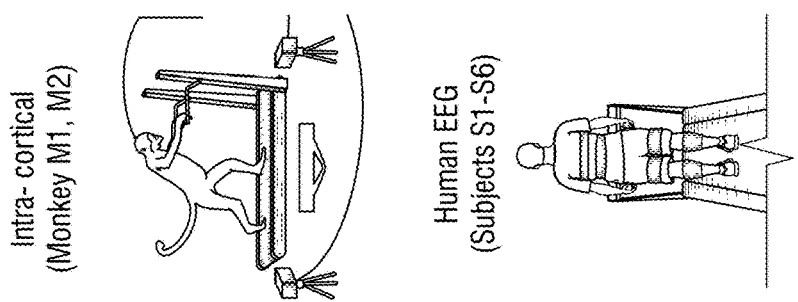
FIG. 2

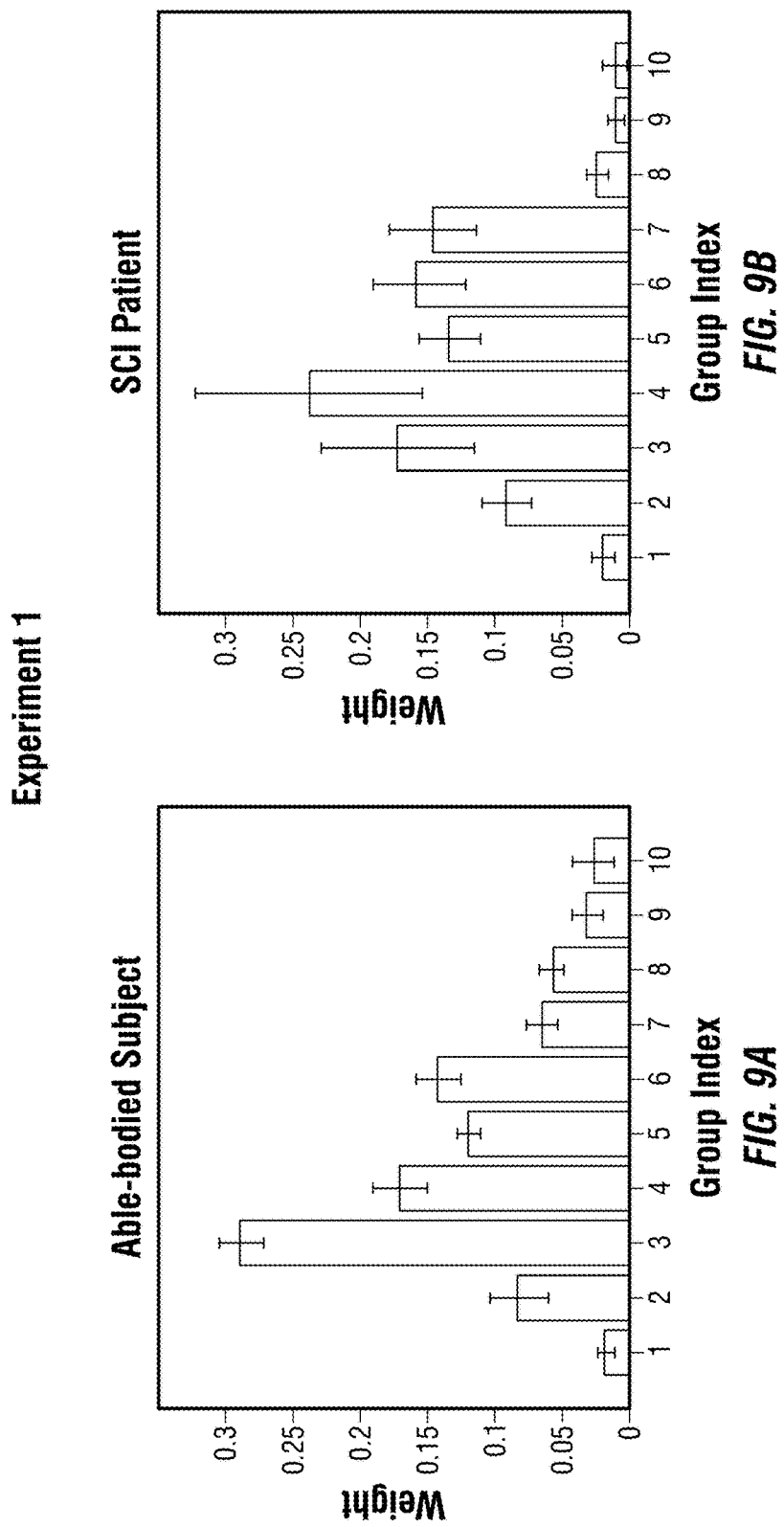

Experiment 2
| | Session | | | | | | | | |
|---|---|---|---|---|---|---|---|---|---|
| | 1 | 2 | 3 | 4 | 5 | 6 | 7 | 8 | 9 |
| OA(%) | 91.36 | 92.44 | 96.36 | 93.58 | 96.42 | 97.47 | 96.60 | 96.83 | 95.11 |
| weight | 0.186 | 0.285 | 0.303 | 0.273 | 0.354 | 0.605 | 0.447 | 0.456 | 0.336 |
*FIG. 11A*
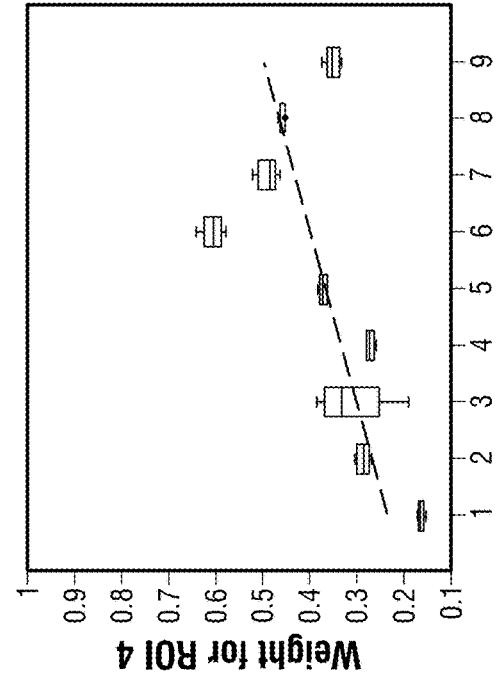
*FIG. 11B*
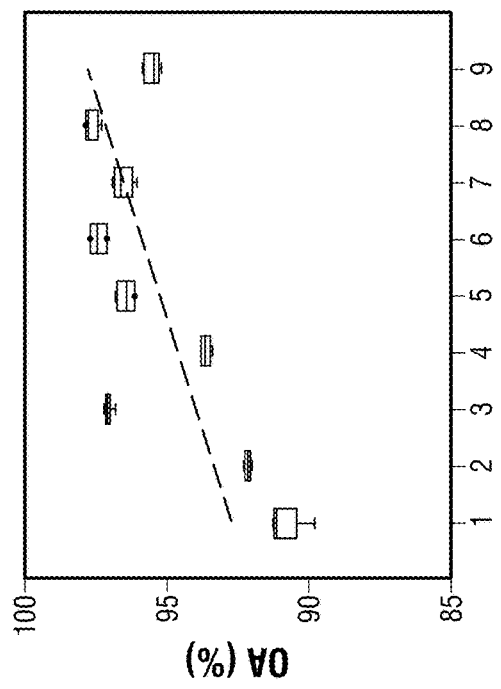
*FIG. 11C*

METHODS FOR CLOSED-LOOP NEURAL-MACHINE INTERFACE SYSTEMS FOR THE CONTROL OF WEARABLE EXOSKELETONS AND PROSTHETIC DEVICES

RELATED APPLICATIONS

This application claims the benefit of U.S. Provisional Patent Application No. 61/842,673, filed on Jul. 3, 2013, which is incorporated herein by reference.

STATEMENT REGARDING FEDERALLY SPONSORED RESEARCH

This invention was made with government support under Grant No. 5R01NS075889 & Grant No. R01 NS081854 from the National Institute of Neurological Disorders and Stroke. The government has certain rights in the invention.

FIELD OF THE INVENTION

This invention relates to a brain machine interface (BMI). More particularly, to systems and methods for acquiring neural signals non-invasively for close-loop control of robotic exoskeletons, prosthetics, virtual avatars or the like.

BACKGROUND OF INVENTION

In 2008, approximately 1.9% of the U.S. population reported some form of paralysis resulting in difficulty or inability to move their arms or legs. Of those, 23% reported being paralyzed due to a spinal cord injury (SCI). There are approximately 12,000 new SCI cases each year. According to The University of Alabama National Spinal Cord Injury Statistical Center and the Centers for Disease Control and Prevention (CDC), the cost of living with SCI can be considerable, and also may vary greatly due to the severity of injury. One recent estimate indicates that SCI alone costs roughly $40.5 billion annually. Providing a system or a method of safe and reliable ambulation and other body movements to these patients would improve quality of life for these patients as well as save on future direct and indirect associated lifetime costs, thereby reducing the socio-economic burden of disability in the US. Moreover, cerebrovascular diseases, or strokes, affect approximately 795,000 people every year in the United States alone, and according to the Survey of Income and Program Participation (SIPP, a survey of the US Bureau of the Census), strokes are a leading cause of serious, long-term disability. With at least 50% of survivors experiencing some hemiparesis, strokes account for the poor physical health and the social dysfunction evident in survivors. Therefore, increasing access to neuro-rehabilitation would consequently increase functional recovery and long-term quality of life (QOL) in these patients, while allowing them greater participation in society. Harnessing brain—machine interfaces (BMI) and robotic-assisted rehabilitation technologies has the potential not only to promote functional restitution through sensorimotor adaptation and central nervous system plasticity, but also to help reduce the socio-economic burden of such disabilities. By adjusting parameters tailored to each individual, his/her state of disability, and goals of intervention, these technologies can provide greater durations of consistent, patient-engaged, repetitive motor practice that consequently allow a physical therapist to work with more patients in the same allotted time. Moreover, BMIs can also be used as a method to measure functional recovery and neuronal plastic changes. Accordingly, there is a need in the art for improved movement assistance systems and biological interface apparatuses to adequately serve these patient populations.

There are a variety of robotic technologies providing robotic exoskeletons or the like. For example, some robotic exoskeletons utilize sensors, such as on a patient's skin, to anticipate desired movements. Other robotic exoskeletons require a patient with a functioning upper body (e.g. hands, arms, and shoulders). Additional robotic exoskeletons utilize external controllers, such as remote controller. In some cases, invasive methods may be utilized to implant neural interfaces utilized for controlling robotic exoskeletons if the benefit-risk ratio is favorable given the surgical risks and complications (e.g., infections or malfunction of the implanted devices) of invasive technologies.

Systems and methods discussed herein may utilize non-invasive scalp electroencephalography (EEG) to acquire neural signals. The neural signals may be provided to a brain machine interface (BMI) that decodes the neural signals into desired motions for an exoskeleton, or to control the movements of a virtual avatar in a motor rehabilitation context or in a gaming application.

SUMMARY OF INVENTION

In one embodiment, a closed loop brain-machine interface system is provided, such as for restoring voluntary motor control in a subject in need thereof. In an embodiment, the subject has lost a degree of voluntary motor control. In an embodiment, the present disclosure also pertains to a non-invasive method of imparting voluntary motor control in a subject in need thereof. Such a method comprises placing externally on the central nervous system of a subject in need thereof a neural signal acquisition apparatus, such as an electroencephalography (EEG). In an embodiment, the method further comprises fitting the subject with an actuator adapted to respond to neural signals with movement. In an embodiment, the actuator may have autonomous robotic control.

In some embodiments, the method comprises collecting one or more neural signals and decoding the neural signal to extract a motor command. In an embodiment, the method comprises transmitting the extracted motor command to the actuator. In some embodiments the method further comprises coordinating the extracted motor command with the manual control of the actuator. In a related embodiment, the method comprises coordinating the extracted motor command with the autonomous robotic control of the actuator or shared control.

In one embodiment, the method may comprise the steps of obtaining brain activity data with an electroencephalography (EEG); transmitting the brain activity data from the EEG to a brain-machine interface (BMI); arranging the brain activity data into a feature matrix; utilizing dimensionality reduction to reduce dimensionality of the brain activity data in the feature matrix; mapping states of a robotic exoskeleton to the feature matrix; and transmitting commands to the robotic exoskeleton, wherein the commands correspond to the mapped states. In some embodiments, dimensionality reduction is performed utilizing a Local Fisher's Discriminant Analysis (LFDA). In some embodiments, mapping of the feature matrix is performed utilizing a Gaussian Mixture Model (GMM). In a further embodiment, the method comprises commanding the movements of a virtual avatar representing a patient that needs rehabilitation of motor function or a user playing a game thru the avatar.

The foregoing has outlined rather broadly various features of the present disclosure in order that the detailed description that follows may be better understood. Additional features and advantages of the disclosure will be described hereinafter.

BRIEF DESCRIPTION OF THE DRAWINGS

For a more complete understanding of the present disclosure, and the advantages thereof, reference is now made to the following descriptions to be taken in conjunction with the accompanying drawings describing specific embodiments of the disclosure, wherein:

FIG. 2 shows decoding of gait kinematics from EEG and intracranial electrodes;

FIGS. 9a-9b show a comparison of weight v. group index for able-bodied subjects and SCI patients respectively;

FIGS. 11a-11c show a table of classification accuracy (OA %) and mean weight of group 4, OA % v. session, and weight v. session respectively;

DETAILED DESCRIPTION

Figure 1:
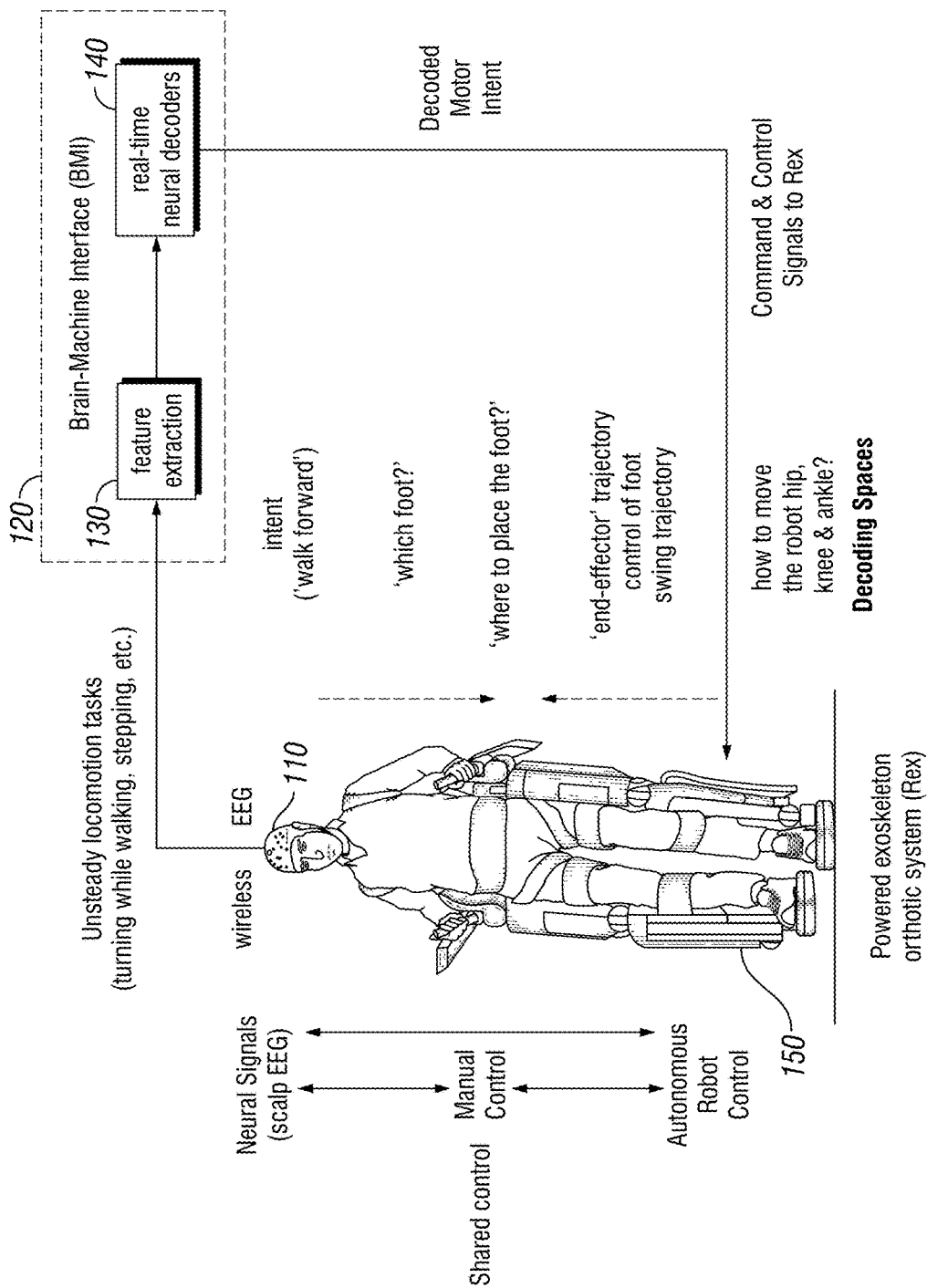
FIG. 1 is an illustrative embodiment of a closed-loop electroencephalography (EEG)-based brain machine interface (BMI) system interfacing robotic exoskeleton.

Refer now to the drawings wherein depicted elements are not necessarily shown to scale and wherein like or similar elements are designated by the same reference numeral through the several views.

Referring to the drawings in general, it will be understood that the illustrations are for the purpose of describing particular implementations of the disclosure and are not intended to be limiting thereto. While most of the terms used herein will be recognizable to those of ordinary skill in the art, it should be understood that when not explicitly defined, terms should be interpreted as adopting a meaning presently accepted by those of ordinary skill in the art.

It is to be understood that both the foregoing general description and the following detailed description are exemplary and explanatory only, and are not restrictive of the invention, as claimed. In this application, the use of the singular includes the plural, the word "a" or "an" means "at least one", and the use of "or" means "and/or", unless specifically stated otherwise. Furthermore, the use of the term "including", as well as other forms, such as "includes" and "included", is not limiting. Also, terms such as "element" or "component" encompass both elements or components comprising one unit and elements or components that comprise more than one unit unless specifically stated otherwise.

Having the potential of increasing the quality of life for paraplegic, tetraplegic, and other disable populations such as stroke patients, Brain-machine Interface (BMI) systems to control lower-body and upper-body exoskeletons have become a focus of research in the past decade. Researchers recently reported the control of external physical devices (robotic manipulators, prostheses) and computer cursors using invasive methods. However, the invasive methods are fraught with problems. Some major limitations of invasive methods are the risks associated with surgery and degradation in signal quality over time.

Non-invasive methods typically acquire brain signals using scalp electroencephalography (EEG). Although having a small signal-to noise ratio compared to the intracortical methods, recent results from our lab show the possibility of using non-invasive (risk-free) decoding of delta-band (low frequency) brain activity using EEG to predict the human limb movements to reliably drive a BMI. The feasibility of a single session training followed by a successful on-line decoding of EEG signals has been demonstrated. Parametric methods such as Kalman Filter, Wiener Filter and soft computing methodologies are used to accomplish high decoding accuracies of limb motion parameters, such as the joint angles and joint velocities. Surface electromyograhic (EMG) and force signals can also be decoded from scalp EEG.

In the last decade, advances in robotic technologies, actuators & sensors, new materials, control algorithms, and miniaturization of computers have led to the development of wearable lower-body exoskeleton robotic orthoses that augment strength, endurance, and/or mobility of humans. There are a number of systems designed to assist or provide walking for stroke patients, spinal cord injured and elderly population such as the Human Assistive Limb Exoskeleton (HAL, Cyberdyne Inc.) and the ReWalk (Bionics Research Inc.).

The Cyberdyne's robot suit HAL is a cyborg-type robot suit that provides a hybrid control system that combines in it a voluntary control system detecting very weak bio-signals from surface sensors on the patient' skin, and a robotic autonomous control system that provides human-like movements by generating torque that produces limb movements that assist the user in performing intended movements. ReWalk, which is currently only suitable for lower-limb mobility impaired adults who have functioning hands, arms and shoulders that allow them to keep balanced using crutches and the ability to stand, enables wheelchair users with lower-limb disabilities to stand, walk, and even climb stairs. RexBionics' Robotic Exoskeleton (Rex) is a self-supporting, independently controlled robotic walking device that enables a person with mobility impairment to stand-up, sit-down, walk, turn, stair-up and stair-down without the need for crutches or walkers. EksoBionics' exoskeleton (Ekso) uses remote control (normally operated by a physical therapist) to signal the left or right leg to step forward, while the user's job, using instrumented crutches, is to balance his/her upper body, shifting the body weight during walking. University of Delaware's active leg exoskeleton (ALEX) that uses a force-field controller, which can apply suitable forces on the leg to help it move on along a desired trajectory. ALEX however is limited to treadmill-based rehabilitation. NASA's X1 lower-limb exoskeleton, initially designed to help astronauts stay healthier in space, may have the added benefit of assisting paraplegics in walking. More recently, Parker Hannifin has licensed the Vanderbilt's powered skeleton and renamed Indego. At 27 lbs, Indego is modular, small and allows users to stand and walk by using sensors that determine if the patient is standing upright, sitting or leaning and perform accordingly.

These robotic rehabilitation systems have the potential to offer individualized therapy, increased efficiency of training at a lower cost, and new sensing capabilities to the physical therapist to quantify patient's progress. Robotic devices that provide feedback to the user, harness user intent, and provide assist-as-needed functionality (e.g., undesirable gait motion is resisted and assistance is provided toward desired motion) may also enhance motor learning and therefore neurological rehabilitation. The availability of safe and reliable robotic therapy can also facilitate intense practice—at a reasonable cost—as well as continuous challenge during rehabilitation, which is known to accelerate recovery and improve rehabilitation outcomes. However, most robotic exoskeleton devices are currently limited to patients with intact upper body function for aided support via crutches (a notable exception is Rex, which does not require crutches for balancing and stability). Moreover, exoskeleton control depends on residual motor signals at the periphery (HAL, ALEX, ReWalk), fine motor control (Rex), or external control via joystick (Ekso); therefore further limiting the type of patients that can benefit from these devices. A common set of challenges for these systems include developing a reliable Brain Machine Interface (BMI) system, shared control issues, the assessment of risk versus benefit, and the regulatory path to follow for use at the clinic and home, cost, and reliability.

A. Reliable BMI Systems

There is a critical need for reliable BMI systems and methods that interpret user intent directly from brain signals and make context-based decisions from the user's current internal state, thus allowing direct and voluntary operation of their exoskeletons beyond their diminished physical, cognitive or sensory capabilities. This involves developing 1) reliable discrete (classifiers) and/or continuous (model-based) neural interfaces to predict the user's intent (at both high and low levels) from EEG; 2) developing BMI-robot systems with long-term prognostic based reliability and fault-tolerant performance, 3) self-calibration, 4) self-diagnostic capabilities with backward-forward failure attribution analysis and error-correction, and 5) suitable behavioral testing methods for reliability and performance assessments of the system. Such BMI systems and methods are discussed further herein.

B. Shared Control

BMI systems should allow for multitasking, require minimal effort and release attentional resources to other cognitive motor tasks. This implies a coordinated effort (shared control) between brain control and autonomous robot control, whereby intelligent robot control algorithms can implement intended user's goals extracted via the BMI system without demanding continuous supervisory control, but rather 'assist-as-needed' control from the neural interface.

C. Safety vs. Benefit

Clinical evaluation requires systematic safety and tolerability assessment of key cardio-metabolic, musculoskeletal, skin, and biomechanical factors along with assessment of neurological and cognitive-behavioral deficit profiles that define the user profile. Cardiopulmonary safety is paramount as individuals with stroke and SCI may have autonomic instability that can alter blood pressure, and their heart rates may not reflect or respond correctly to increased cardiopulmonary demands, depending on the lesion level and completeness. The cardiopulmonary demands of steady state and sustained BMI-Robot usage must be initially assessed and carefully monitored for two further reasons: the mean peak cardiovascular fitness levels after spinal cord injury vary considerably depending on the lesion characteristics, but are generally much lower than normal; and skeletal muscle after SCI (or any CNS injury such as stroke) shifts in a deficit severity dependent manner from slow twitch to a fast twitch molecular phenotype, which predisposes to anaerobic metabolism, reduced insulin sensitivity, and oxidative injury. Patients with abnormal gait biomechanics, anaerobic muscle metabolism, and fitness levels similar to those in heart failure patients must show adequate cardiopulmonary tolerance based on subject perceived exertion scales, and objective monitoring of cardiopulmonary and metabolic profiles. These metabolic measures, along with careful clinical surveillance and blood markers to assess for muscle injury are key parameters for validating cardiopulmonary, metabolic, and muscle safety during exoskeleton use.

Rehabilitation clinician-scientists are highly aware that robotics may impose unusual joint kinetics and kinematics that could potentially injure bone or skin, particularly in SCI or stroke populations that characteristically have accelerated osteopenia or osteoporosis, unusual spasticity patterns, abnormal movement synergy patterns, or contractures. Systematic screening for bone health using dual X ray absorptiometry and assessment ahead of time for "hot spots" of abnormal torque or impulses that could predispose to injury is vital to safe utilization. While impedance control and torque cut-offs successfully assure safety in lower extremity robotics, cumulative experience is limited for mobility devices, warranting caution and careful consideration between engineers, clinicians, and individuals with neurological disability to appropriately apply this exciting new technology.

D. Reverse Engineering the Brain

A better understanding of the neural representations, at the cortical level, for action and perception of bipedal locomotion is essential for evaluating changes in cortical dynamics during rehabilitation using closed-loop BMI systems, and assessing how these changes are correlated with gait adaptation induced by BMI-robot therapy.

In an embodiment, the BMI system discussed herein relates to a shared control architecture that benefits from the control of definitive parameters of walking by an actuator, or an exoskeleton system. In some embodiments the BMI coordinates brain control (intent), with the manual control of an actuator (when available) and the autonomous robotic control algorithm of an actuator to translate intent into locomotion. In an embodiment, the BMI system uses the Robotic Exoskeleton (REX, REX Bionics Ltd.). One advantage of this system is that it is self-balancing and it has a variety of preprogrammed motions, the most important being the walking, turning, sitting, standing motions. The use of any physical or virtual actuator, exoskeleton, external device, or a prosthetic limb with the BMI system is contemplated herein. The term "actuator", "exoskeleton", "prosthetic limb", or an "external device" is used interchangeably and mean any kind of device, physical or implemented in software (e.g., virtual reality) adapted to perform a movement. Although, an actuator performs a movement in three dimensions, an actuator can also be limited to performing a movement in two dimensions or a single dimension. A preferred actuator comprises a prosthetic limb, which can be fitted on, or integrated into, the body of a subject. An actuator may also be associated with machinery and/or circuitry that allow the actuator to respond to one or more forms of input with one or more movements.

FIG. 1 is an illustrative embodiment of a BMI system. An EEG 110 may be coupled to BMI 120. As a nonlimiting example, the EEG 110 may be wirelessly coupled to the BMI 120. The EEG 110 may be any Electroencephalography (EEG) device suitable for recording electrical activity along a user's scalp, such as a 64-channel electrode cap (actiCAP, Brain Products, GmbH). The BMI 120 may comprise a feature extraction 130 and neural decoder 140 modules. Feature extraction 130 module may receive and process data from EEG 110. In some embodiments, feature extraction 130 module may filter and/or standardize data from the EEG 110. In some embodiments, feature extraction 130 module may be utilized to generate a feature matrix. A feature (or feature vector) of neural signal is a quantity based on (EEG) measurements that relates to the current cognitive task of the user. A feature may be composed of the collection of information from several electrode locations. This quantity may be the time course of signals for a specified time window, concatenated for several electrode locations, which can be designed to capture the synchronized/desynchronized amplitude modulation/demodulation of the EEG signals from multiple electrode locations, for single and/or multiple frequency bands. In some cases, a feature may be the collection of spectral power information from several electrode locations. A feature may also be a mixture of time and spectral power information for single or multiple frequency bands. A feature matrix is the time evolution of a feature during a single cognitive task and/or collection of cognitive tasks all together. Thus, feature matrix contains filtered and extracted EEG data that is relevant to desired limb movements or motor intent of a user wearing the EEG 110.

The feature matrix produced from the EEG data may yield a high dimensional set making it desirable to reduce dimensionality. A dimensionality reduction method should keep task related information, embedded within the feature matrix intact, while providing lower, dimensionally-condensed information for real-time fast computations and improved discrimination between different task related information. Neural decoder 140 modules may perform dimensionality reduction of the feature matrix. Any suitable dimensionality reduction techniques may be utilized, such as Local Fisher's Discriminant Analysis (LFDA). Task related information can be visualized as high dimensional clouds or groups of data points. Classification of tasks means that the clouds related to different tasks must be discriminated. Although one task can be represented by a cloud, it can also be a collection of several sub groups, altogether representing the task related information. One advantage of the LFDA method is that it preserves this local grouping information (or minimizing the within class separability), as well as different task related grouping information in a larger scale (or maximizing between class separability). The neural decoder 140 modules may also employ a Gaussian Mixture Model (GMM) classifier to map the states of the robotic exoskeleton to the feature matrix. A GMM classifier has the ability to fit a single Gaussian distribution or a multiple Gaussian distribution to the reduced dimensional data, as needed, to best represent a model for different task related information, thereby allowing the BMI 120 to decode motor intent and transmit command/control signals to a robotic exoskeleton 150 coupled to the BMI. For a real-time control, the feature extraction steps are repeated as listed. Dimensionality reduction of the feature vector is performed using the LFDA parameters obtained from the training data. Also, the GMM model is evaluated using the parameters obtained from the training data. The result obtained from the GMM evaluation in real-time are the probabilities of the current feature vector belonging to the classes (or type of exoskeleton motion such as walk, stop, sit, stand, turns, etc.). The class which has the maximum probability is then selected as the command that is to be transmitted to the exoskeleton to execute that type of motion, hence allowing the user to command the exoskeleton in the BMI framework.

Wireless EEG systems, sophisticated machine learning, system identification methods, and shared control approaches to minimize cognitive effort (and allow multitasking) may be deployed to calibrate the neural interface, control the powered exoskeleton and to reverse-engineer the neural representations for gait production. The BMI will coordinate among brain control (intent), manual control (when available), and the autonomous robot control algorithms. Decoding spaces for BMI control are shown. The possibility of decoding the intended user motion rather than the motion parameters using an exoskeleton (e.g., REX) and performing an inherent closed-loop control once a motion command is received is disclosed herein. This requires a classifier approach of decoding compared to the mapping of EEG signals to continuous set of joint parameters. In an embodiment, the present disclosure pertains to a decoding model architecture and a decoding model for repeated walking—turning right—turning left motions and sit-rest-stand motions. In some embodiments, the present disclosure relates to an EEG-based BMI system to control the REX (NeuroRex) exoskeleton in a real-time closed-loop setting, resulting in independent walking for the paraplegic user. The term "motor command" means one or more neural signals associated with the control of one or more muscles or muscle groups of a subject. Motor commands are generally formed in the brain or nervous system of a subject and these commands control movements executed by the muscles of the subject. Movements preferably comprise voluntary movements, however movements may also comprise involuntary movements.

The term "subject" means any individual using or employing the invention disclosed herein for any purpose. As used herein, the term "subject" need not refer exclusively to human beings, but rather the term encompasses all organisms suffering from some degree of loss of motor control. Preferably, the term refers to mammals and more preferably to humans.

The present disclosure, in some embodiment, provides the first BMI-capable robotic exoskeleton that can interpret user intent to assist a mobility-impaired person to walk independently without the need for additional support or crutches.

Applications and Advantages

The closed loop brain-machine interface and the disclosed methods represent a significant advance in the fields of neural, cognitive and rehabilitation engineering, neurology and bioengineering. The closed loop brain-machine interface provides, for the first time, a non-invasive system by which an actuator can be controlled directly by signals originating in the brain of a user, and by which sensory feedback is transmitted from the actuator, directly or indirectly, to the user. In the case of a BMI system to an exoskeleton such as REX, motion of the actuator is transmitted via the physical human-machine interface (e.g., robot is securely attached to the human via straps and harnesses) to the user so that his/her body and sensory organs can interpret the motion. In another embodiment, the states of the actuators could be reflected on the user via vibrations, surface functional electrical stimulation (FES) and tactors placed on the user's body. In another embodiment, feedback is provided to the user by means of a visual display (e.g, smartphone, or small screen/display attached to the exoskeleton or the user's glasses). In another embodiment, feedback is provided to the user via single/multiple tone audio information, related to the task, and/or the dynamic environment in which the user moves in.

The closed loop brain-machine interface can greatly enhance the quality of life of subjects who have lost a degree of motor control or who have lost the use of one or more given appendages. These subjects can be fitted with the disclosed invention, imparting the ability to control external devices via brain-derived signals. The invention of the present disclosure can allow disabled subjects to not only control an actuator, but it can also permit these patients to perform a range of activities many take for granted, such as walking. The invention of the present disclosure may also assist those subjects who, prior to implementation of the present invention, might have never walked or been able to perform tasks with their hands or arms.

Brain-Machine interface (BMI) systems allow user to control external mechanical systems using their thoughts. Previous methods have used invasive techniques to acquire brain signals and decode user's intended motions to drive these systems (e.g., a robotic manipulator). In some embodiments, the present disclosure pertains to using a lower-body exoskeleton and measuring the user's brain activity using non-invasive electroencephalography (EEG). In some embodiments, the brain activity of the user is then processed and decoded by the BMI to determine the user's desired motor intent. Command and/or control signals corresponding to the desired motor intent may be transmitted to a robotic exoskeleton to provide the user with the ability to make the intended motion. In some embodiments, the present disclosure relates to a system for translational clinical brain-machine interface (BMI) roadmap for an EEG-based BMI to a robotic exoskeleton. In an embodiment, the present disclosure pertains to methods of validation of an intelligent self-balancing, robotic lower body and trunk exoskeleton (Rex) augmented with EEG-based BMI capabilities to interpret user intent to assist a mobility-impaired subject to walk independently. The goal is to improve quality of life and health status of a mobility impaired subject by enabling standing and sitting, walking and backing, turning, ascending and descending stairs/curbs, and navigating sloping surfaces in a variety of conditions without the need for additional support or crutches.

Although the present disclosure does not directly treat a condition giving rise to paralysis or other loss of motor control, the closed loop brain-machine interface offers disabled patients, for the first time, a new option for dealing with their condition. For example, a paralyzed patient no longer need be confined to a wheelchair or to a bed; the disclosed invention might afford this patient the opportunity to walk again or perhaps for the first time. In another embodiment, the disclosed invention affords a person lacking motor control over his or her arms and/or hands, the ability to move one or more actuators as the patient would move his or her own appendages. Moreover, since the disclosed invention comprises a closed loop, the closed loop brain-machine interface also enables a patient to "feel" and interact with his or her environment in a way heretofore unavailable to the patient.

The use of the systems and methods disclosed herein can be considered to be an augmented form of Locomotor Therapy (LT). LT, implemented by weight-supported treadmill walking facilitated by manually assisted movements of the subjects' legs by 2 therapists, or by a robotic device such as the Lokomat, has been shown to improve walking measures and balance in AIS C and D subjects in controlled studies. Uncontrolled reports of improvement in orthostasis, vital capacity and bowel and bladder have been given with the use of LT and the use of REX.

Summarily, the closed loop brain-machine interface embodies, among other things, a significant advance for patients suffering from impaired motor control over their appendages. The disclosed invention can greatly enhance the quality of life for these patients and can be a benefit for caregivers as well.

Additional Embodiments

Reference will now be made to various embodiments of the present disclosure and experimental results that provide support for such embodiments. The following examples are included to demonstrate particular aspects of the present disclosure. It should be appreciated by those of ordinary skill in the art that the methods described in the examples that follow merely represent illustrative embodiments of the disclosure. Those of ordinary skill in the art should, in light of the present disclosure, appreciate that many changes can be made in the specific embodiments described and still obtain a like or similar result without departing from the spirit and scope of the present disclosure.

Human Subjects:

The first step is to determine the sensory-motor profile of two classes of individuals, those with paraparesis and those with complete paraplegia whose locomotion can be enhanced by the use of Rex. That is, the severity and neurological segmental levels of motor and sensory deficits that an individual must have to: 1) Benefit from the use of a BMI system discussed herein (e.g. whether repetitive training and use of the system leads to gains in mobility, health and quality of life); and 2) be capable of interacting with BMI system to achieve useful mobility. Of particular importance is knowledge of the strength required for maintaining an erect posture in the exoskeleton, the strength required in muscles of the legs, hips, trunk, shoulders, arms, hands and neck. It is also important to determine if BMI control of a robotic exoskeleton provides additional functionality (e.g., multitasking, increased cortical plasticity leading to shorter sensorimotor intervention periods) for individuals who are able to control a robotic exoskeleton using hand controls.

Thus, comprehensive clinical assessments were performed to ensure safety, assess the extent of cognitive-motor-body adaptations during robot use, and determine whether BMI systems discussed herein can replace hand controls and/or cooperate with a robotic exoskeleton's embedded autonomous control schemes to decrease user's cognitive load.

B. Research Design and Methods

B1. Primary Outcomes:

1. Maximum degree of motility achieved in:
   a. Standing from a sitting position. Measure: time to complete action.

b. Walking in a straight line. Standardized tests: Measure: 6 minute walk; 10 m walk.
c. Turning right and left: Measure: modification of the 6 minute and 10 m walks.
d. Navigating obstacles: Measure: time, number of errors.
e. Stand-to-sit and sit-to-stand: Measure: time to complete; errors.
f. Climbing, descending stairs. Measure: time to complete, errors.

2. fMRI-EEG Identification of the Neuroanatomical Sources of Brain Signals for BMI Control of a Robotic Exoskeleton.

Two approaches have been taken with respect to the brain signals used to control the movement of a robotic exoskeleton: (a) Recording from neurons in the sensory-motor cortex whose firing can be time-linked to the desired movement, and is predictive of gait kinematics; (b) Recording patterns of the scalp EEG from broad areas of the cortex and correlating them with the desired movement, which is the approach for the BMI system discussed herein (FIG. 2). As shown in FIG. 2, decoding accuracies (Pearson's r) of non-invasive (EEG) as compared with intra-cortical (spikes-based) neural decoders for inferring gait parameters demonstrate the feasibility of designing noninvasive BMI systems for command and control of robotic exoskeletons. The successful use of this method indicates that information linked to movements is widely distributed throughout the brain. The present disclosure correlates scalp recorded EEG activity with functional BOLD signal magnetic resonance imaging (fMRI) activation and de-activation of cortical and subcortical areas during willed movement. The motor paradigm of initiating a step with leg flexion is first investigated. Subsequently stepping movements are imitated by using a recumbent cycling pedaling apparatus.

3. Time-Resolved Examination of how Cortical Networks May Adapt to Changes in the Neural Representation of Gait Due to NeuroRex Use.

Human locomotor studies involving patients with stroke and SCI suggest that bipedal interlimb coordination requires some level of cerebral control. Patients with cerebral damage from stroke show problems in interlimb phasing resulting in asymmetric walking patterns. Split-belt treadmill adaptation experiments have shown that right and left legs can be trained individually in healthy subjects, for example, by training subject's legs to walk at different speeds in the same or different directions. This type of manipulation results in early asymmetric walking as interlimb coordination is phase shifted and step lengths become asymmetric not unlike walking with a 'limp'; however, with practice subjects can improve phasing and reduce gait asymmetries. Analyses of after effects showed that locomotor training is both leg- and direction-specific. Other have shown that split-belt adaptation partially transfers to over ground walking in patients post stroke, and then it could have implications for the restoration of gait function in these patients.

Experimental Protocol:

Although the robotic exoskeleton or REX system can be controlled via a joystick by the user, in Task 1 subject is asked to follow and complete a path marked on the ground while exoskeleton is controlled by an operator remotely. The rationale behind this task is to have the user focus only on the given walking-turning right-turning left task while minimizing the effect of the subject's hand/finger motions on the data set gathered from the EEG. The path is a discrete number 8 figure where each linear section's connection angles are compatible with the robot's right/left turn angles.

Task 2 was conducted with the remote control interface for repeated sit-rest-stand-rest cycles for 5 minutes.

Data Acquisition and Pre-Processing:

A 64 Channel electrode cap (actiCAP, Brain Products GmbH) was placed on the head of the subject according to the international 10-20 system having FCz as reference and AFz as ground. A wireless interface (MOVE system, Brain Products GmbH) was used to transmit data (sampled at 100 Hz) to the host PC. Data then filtered in the (0.1-2 Hz) range using a 2nd order Butterworth filter. Filtered data were then standardized (z-score). Separate channels were then used to create a feature matrix (to extract the EEG delta-band amplitude modulation information) using a 200 ms window with 1 shift, each row having the time shifted from $[ch_1(t-n); \ldots, ch_1(t); ch_2(t-n); \ldots, ch_2(t) \ldots ch_m(t)]$, where n is the window size in samples and m=64 is the total number of channels.

Classification Method for Decoding:

Having such a feature matrix structure often yields a high dimensional set (for all 64 channels used, the set is 1280 dimensional). Some techniques used for dimensionality reduction may include Principal Component Analysis (PCA) or Fisher's Linear Discriminant Analysis (LDA), which work under the assumption that the distributions are Gaussian, whereas real-life observations are often non-gaussian and in some cases are multimodal. The BMI system may use a classification paradigm that was designed to preserve and use the rich statistical structure of the data. The BMI system may use a Local Fisher's Discriminant Analysis (LFDA) to reduce the dimensionality of the data while preserving the multimodal structure, and employ a Gaussian Mixture Model (GMM) classifier to map the states of the exoskeleton to the feature matrix (amplitude modulation of the subject's delta-band brain activity).

1) LFDA: For a data set with samples $X=\{x_i\}^n_{i=1}$ in $R^d$ (d is the dimension of the feature space, n is the total number of samples), and class labels (in our case: the motion states) $y_i \in \{1; 2; \ldots c\}$ (c is the number of classes), the affinity (heat kernel) between $x_i$ and $x_j$ is defined as:

$$A_{i,j} = \exp\left(-\frac{\|x_i - x_j\|^2}{\gamma_i \gamma_j}\right) \quad (1)$$

which measures the distance among data samples. Here $\gamma_i = \|x_i - x_i^{(knn)}\|$ denotes the local scaling of data samples in the neighborhood of $x_i$, and $x_i^{(knn)}$ is the $k_{nn}$ nearest neighbor of $x_i$. In LFDA, the local between class and within class scatter matrices ($S^{lb}$ and $S^{lw}$) are defined as:

$$S^{lb} = \frac{1}{2} \sum_{i,j=1}^{n} W_{i,j}^{lb}(x_i - x_j)(x_i - x_j)^T \quad (2)$$

$$S^{lw} = \frac{1}{2} \sum_{i,j=1}^{n} W_{i,j}^{lw}(x_i - x_j)(x_i - x_j)^T. \quad (3)$$

$W^{lb}$ and $W^{lw}$ are, $$W_{i,j}^{lb} = \begin{cases} A_{i,j}(1/n - 1/n_l), & \text{if } y_i = y_j = l \\ 1/n, & \text{if } y_i \neq y_j \end{cases}$$

-continued $$W_{i,j}^{lw} = \begin{cases} A_{i,j}/n_l, & \text{if } y_i = y_j = l \\ 0, & \text{if } y_i \neq y_j \end{cases}$$

where is the number of training samples for the $l^{th}$ class. Thus the transformation matrix ($T_{LFDA}$) to reduce the dimensionality of the feature space is defined as $$T_{LFDA} = \arg\max_{T_{LFDA}} tr[\Psi_{lw}^{-1}\Psi_{lb}] \quad (4)$$

where $\Psi_{lw} = T_{LFDA}{}^T S^{lw} T_{LFDA}$, $\Psi_{lb} = T_{LFDA}{}^T S^{lb} T_{LFDA}$ and $S^{lb} T_{LFDA} = A S^{lw} T_{LFDA}$ for diagonal eigenvalue matrix A.

Defined by the offline analysis, this transformation matrix was used to reduce the dimensionality of the feature matrix formed in real-time.

2) GMM: A Gaussian mixture model is a combination of two or more normal Gaussian distributions. A typical GMM probability density function is defined as:

$$p(x) = \sum_{k=1}^{K} \alpha_k N\left(x, \mu_k, \sum_k\right) \quad (5)$$

$$\text{where } N\left(x, \mu_k, \sum_k\right) = \Gamma \exp\left(-\frac{1}{2}(x-\mu_k)^T \sum_k{}^{-1}(x-\mu_k)\right)$$

$$\text{for } \Gamma = \frac{1}{(2\pi)^{d/2}|\sum_k|^{1/2}}.$$

The mixing weight $\alpha_k$, means $\mu_k$ and covariance matrix $\Sigma_k$ are estimated by the expectation maximizing algorithm. As for the transformation matrix for the dimensionality reduction, these parameters were identified in the offline analysis and used to estimate, in real-time the probabilities of a given feature vector belonging to one of the classes. A more detailed discussion of LFDA-GMM dimensionality reduction is provided in Li et al, "Locality-preserving dimensionality reduction and classification for hyperspectral image analysis," *IEEE Transactions on Geoscience and Remote Sensing*, Vol. 50, no. 4, pp. 1185-98, 2012.

The offline analysis results for training GMM distribution for two different cases are reported (task 1 and task 2), where the subject was asked to attempt in his or her mind the walk, turn-right, turn-left motions, and sit-down, rest, stand-up motions.

Figure 3:
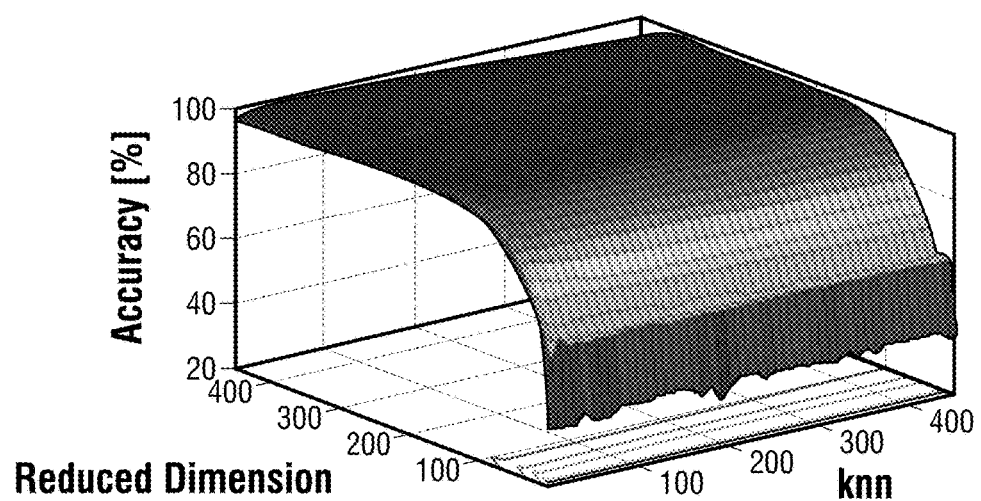
FIG. 3 shows accuracy surface for task 1 gridded for 451 reduced dimension and 451 knn values.
Figure 4:
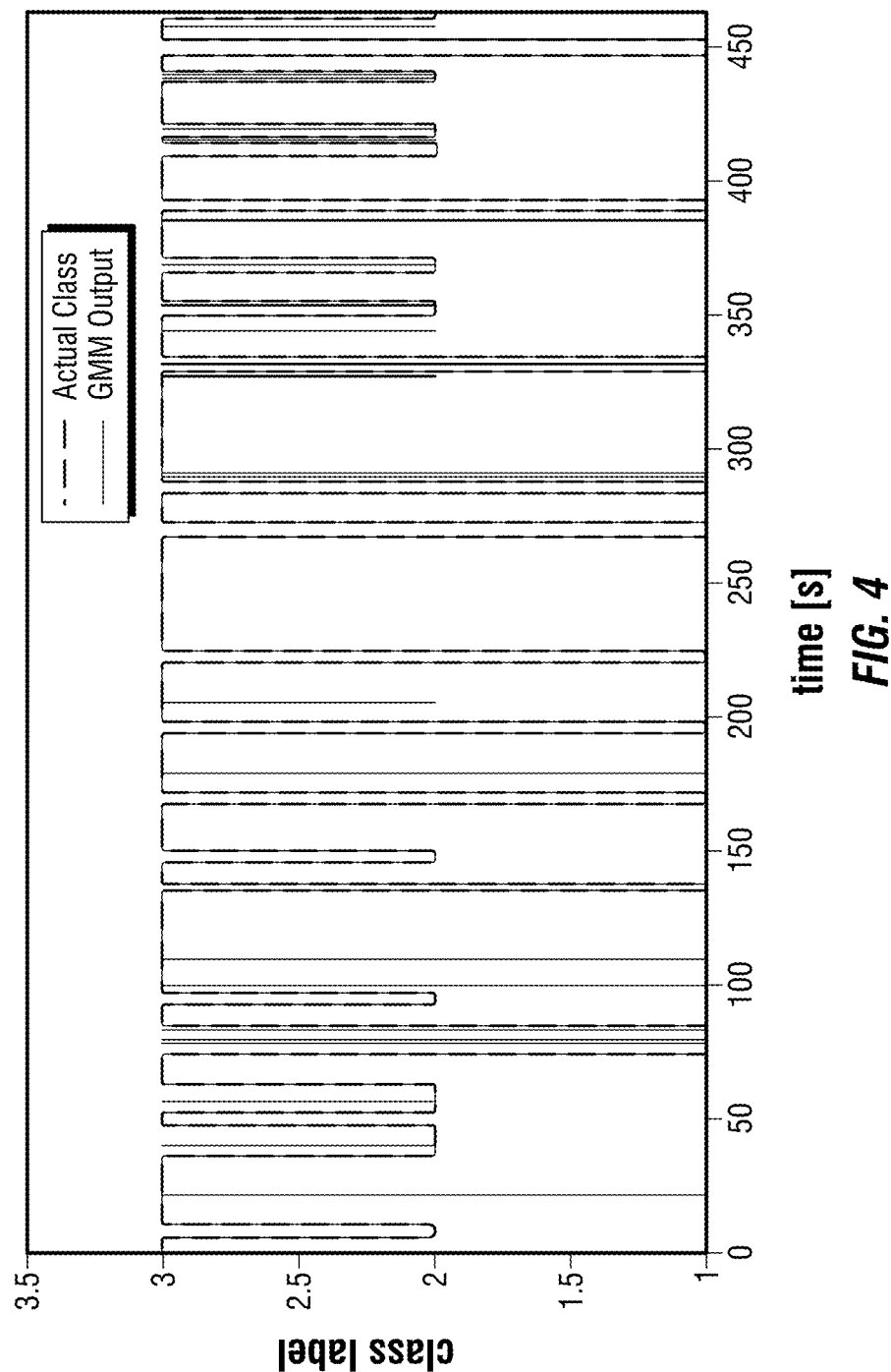
FIG. 4 shows evaluation of the task 1 model using the entire data set.
Figure 5:
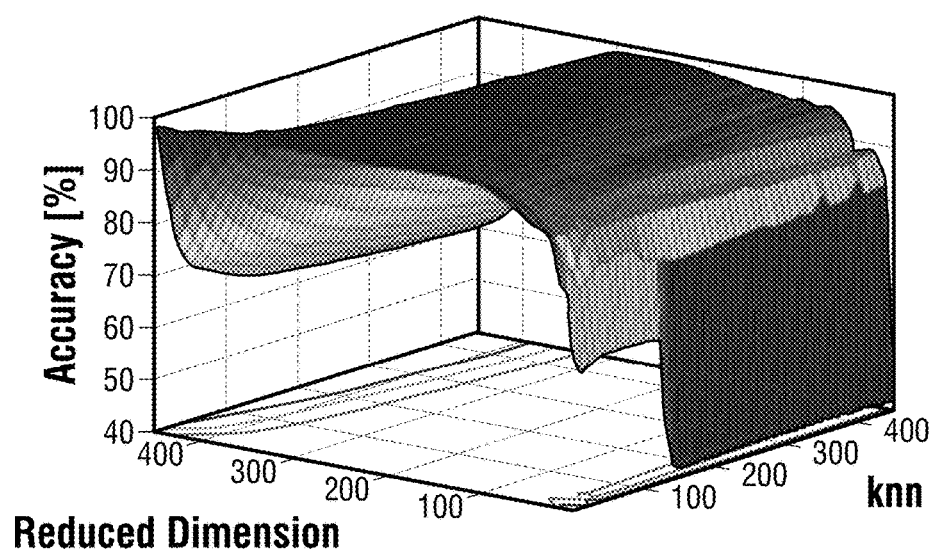
FIG. 5 shows accuracy surface for task 2 gridded for 451 reduced dimension and 451 knn values.
Figure 6A:
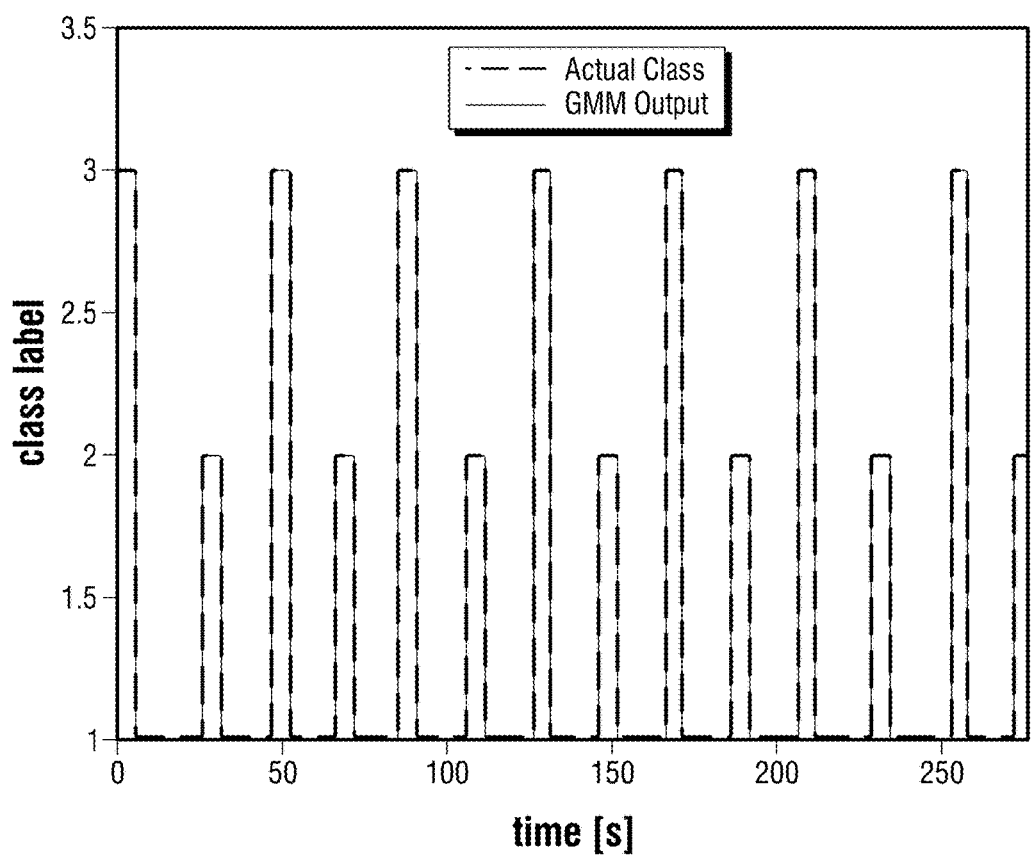
FIG. 6a shows evaluation of the task 2 model using the entire data set.

Open-Loop Analysis:

EEG decoding methods discussed herein to identify the user intent provided a good performance for a range of reduced dimensionality and k-nearest-neighbor (knn) parameters. After the pre-processing step, the feature matrix data of different classes was grouped (3 classes for the tasks reported). 1500 samples for training were randomly selected, and from the remaining data, random 1500 samples for testing, from each class. This corresponds to 9.7% and 16.2% of the total data length for tasks 1 and 2 respectively. FIG. 3 shows the validation accuracy surface for varying dimension and knn values (1 to 451 for both). The accuracy for this case is sensitive to the reduced dimension, but less sensitive to the knn value. The mean accuracy change from reduced dimension 51 to 81 for all knn values is an increase of 12.93%, whereas a knn change from 1 to 81 (where the maximum accuracy of 99.07% occurs) for all dimensions yields a mean accuracy increase of 1.39%. Using fixed reduced dimension and knn parameters which yield high accuracies, the whole data set was evaluated using the corresponding GMM distribution. This validation step was designed to be a pseudo real-time implementation. Namely, the specified windows size of data were read from the pre-processed data and the probabilities of the feature vector belonging to each class were calculated, identifying the class label as the one with maximum probability. FIG. 4 shows this test of evaluating the entire data set using the LFDA-GMM method. The overall accuracy associated with this case is 98.17%. These analyses were repeated for a second case study using the data set from task 2. Similarly, the accuracy surface over iterated knn and reduced dimension values are shown in FIG. 5. The associated pseudo real-time estimation is reported in FIG. 6a. The overall accuracy associated with this test is 99.68%.

Closed-Loop Implementation:

Closed-loop implementation sessions comprise two steps. One for data acquisition, dimensionality reduction and GMM model training, and one for closing the loop in real-time and simultaneously recording the related EEG activity for future analysis. Having identified average values that yield low dimensions (around 80) and high accuracies (around 93%), the model training and offline validation to confirm accuracy takes on average 45 seconds.

A multi-threaded C++ code was developed for the closed loop implementation of the method that has a thread for the real-time EEG data acquisition and another thread for the data preprocessing and GMM evaluation. It should be noted that this closed-loop implementation includes the user in-the-loop by obtaining brain activity data from the user with the EEG. The data acquisition thread continuously receives the EEG data and saves it in a data file. In contrast to other systems that gather data from certain regions of the brain, such as systems utilizing electrodes implanted in certain regions, significant amounts of data may be obtained from the EEG. As such, it may be desirable to dimensionally reduce the obtained data and classify the data so that the data can be properly associated with desired motor functions. After receiving a specified window size of samples, the data matrix is passed to the second thread. The second thread is responsible for pre-processing the data by filtering it using a 2nd order Butterworth filter between [0.1 2 Hz] using the overlap-add technique, forming the feature vector, standardizing it and performing dimensionality reduction using the identified transformation matrix (equation 4). This thread is also responsible for calculating the probabilities of the feature vector belonging to each class and identifying the class label as the one with maximum probability. It also converts the class label to the associated motion of the exoskeleton (stop or walk forward) and transmits it wirelessly to the exoskeleton via the RS232 protocol.

As an initial study focus was directed on a relatively simpler task of walking or stopping with the exoskeleton. In a single session an increased voluntary control of the exoskeleton by the subject after several trials with the same model was observed. After performing four exploratory trials with the exoskeleton, the subject reported that he was able to stop the exoskeleton and walk again with it repetitively at least three times in a three minutes long trial. Additionally, the subject was asked to stop the robot and stay standing for as long as he can, as the model's output of walk or stop continuously was recorded.

In total 8 trials were conducted. Each trial lasted until a total of 5 stops were achieved. The percentage of the stop signals transmitted to the exoskeleton was calculated from the total length of the recorded commands. For the first 4 trials recorded, the percentage of stops was increased from 97.11% to 99.32%. Following a break of 45 minutes after the $4^{th}$ trial, a monotonic decrease of 1.15% was recorded, followed by an increase of 1.52%, bringing the accuracy to 99.69% for the last trial. The reason for the decrease may be an inherent time delay of the exoskeleton. As described before, the exoskeleton was designed to be stable, it thus has to complete a whole cycle of gait before stopping, resulting in a slow time response compared to the model's output. The exoskeleton's full stops were also timed manually and the percentage of stops was calculated from the overall experiment duration.

A monotonic increase of accuracy from 21% to 70% was observed over the first period of trials, and a final accuracy of 90% for the last trial. The next step is to account for this time delay thus increasing the exoskeleton's response to the timed commands recorded from the model's output. It should be noted that a total of four sessions with the subject were run and the increased number of correct responses is a step closer towards an implementation including several tasks (walking, stopping, turning right and left, sitting and standing).

Figure 6B:
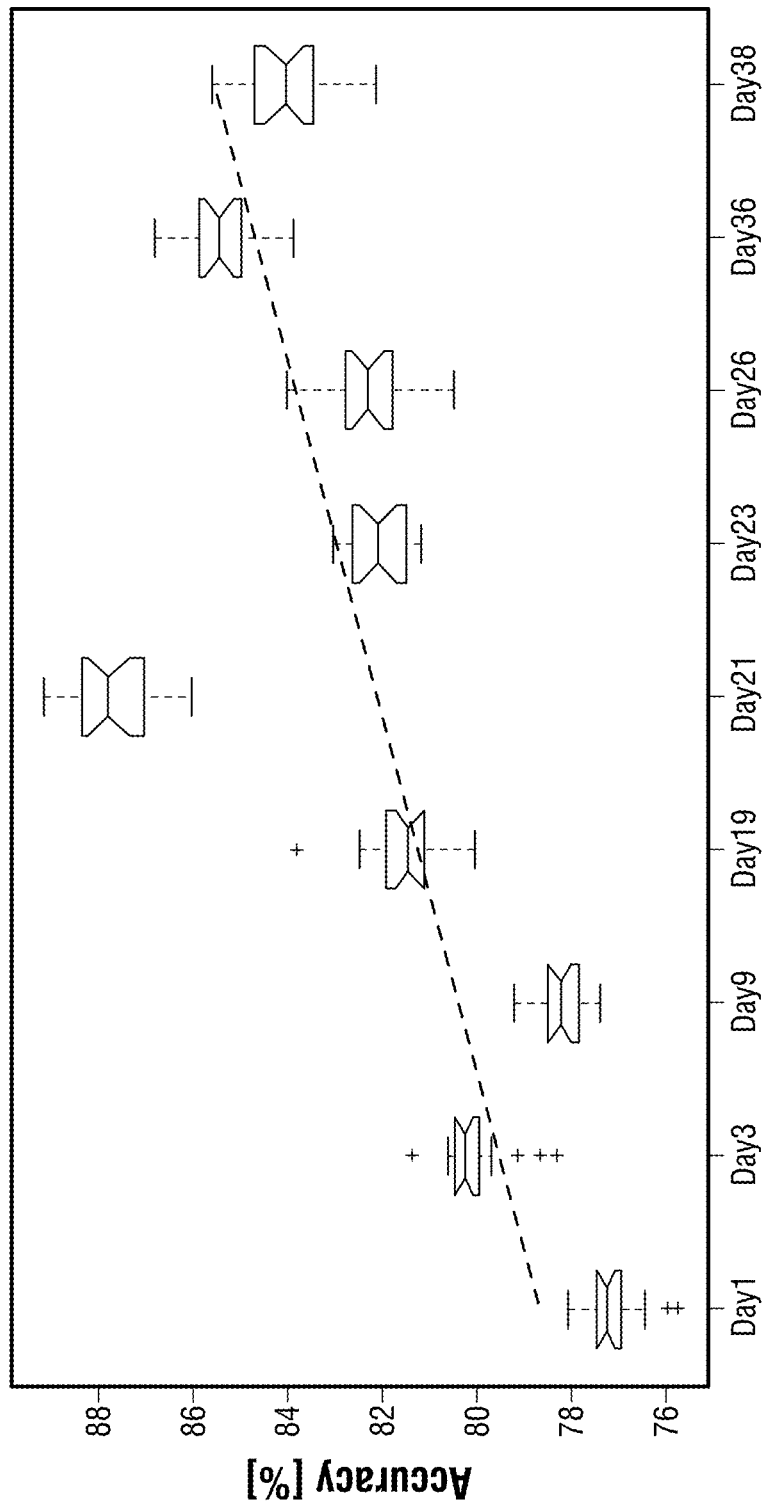
FIG. 6b shows decoding accuracy over 9 sessions.

Having the locality preserving dimensionality reduction combined with a multimodal GMM classification indeed performed very well for a range of control parameters. A series of offline cross validation tests were also performed to check the performance of the decoder method disclosed herein. A single model was tested in an iterative setting for 1500 test samples randomly selected for each of the 20 iterations. The mean accuracy observed from this test was 97.74±1.2% for task 1 and 99.31±0.54% for task 2. The model generated for task 1 with the data from task 2 (each having 3 classes) was also tested as an additional control. A mean accuracy of 18.78% was observed for this case, and a mean accuracy of 8.9% was observed for the case when the task 2 model with the task 1 data was tested. This suggests that the models disclosed herein are extracting EEG features unique to the tasks for which they were originally trained for. Using the proposed decoding methodology, an increase of correct command executions over trials can clearly be seen. In the closed-loop setting disclosed herein, more successful trials were seen when using an on-site trained model compared to a model that is trained in a previous session. That brings the importance of a more adaptive learning scheme (identifying and updating the parameters as the experiment is performed). It should also be noted that the overall control scheme encapsulates the subject's adaptation to a given task, thus a longitudinal study investigating the control performance of a fixed model over sessions is also important. A 9 sessions study spanning 38 days was conducted to analyze this adaptation. Decoding parameters are identified using the Session-1 data, conservatively for 20% training and 20% testing samples, and kept fixed for the remaining sessions. Training and testing samples are selected randomly, for each session, 10 times to account for possible decoder over fitting. FIG. 6b summarizes the results. Median accuracy over 10 iterations for day-1 is 77.24%. The trained model for day-3 yields and accuracy of 80.25% and for day-38 the final accuracy is noted as 84.03%, while the maximum accuracy is 87.77% for day-21. A linear curve fit to the medians of session accuracies (dotted line) reveals the increase of decoding accuracies over the 9 sessions. As noted, optimal decoder parameters were determined from Day-1 training data, and kept fixed over sessions. Only 20% of the data were used for training. Box plots show each session's training for randomly selected training data over 10 iterations. Having fixed parameters for the model and increasing accuracy over sessions suggests changes in the recorded EEG data, meaning a change in brain wave patterns and/or amplitudes and/or locations, suggesting cortical plasticity.

Figure 7:
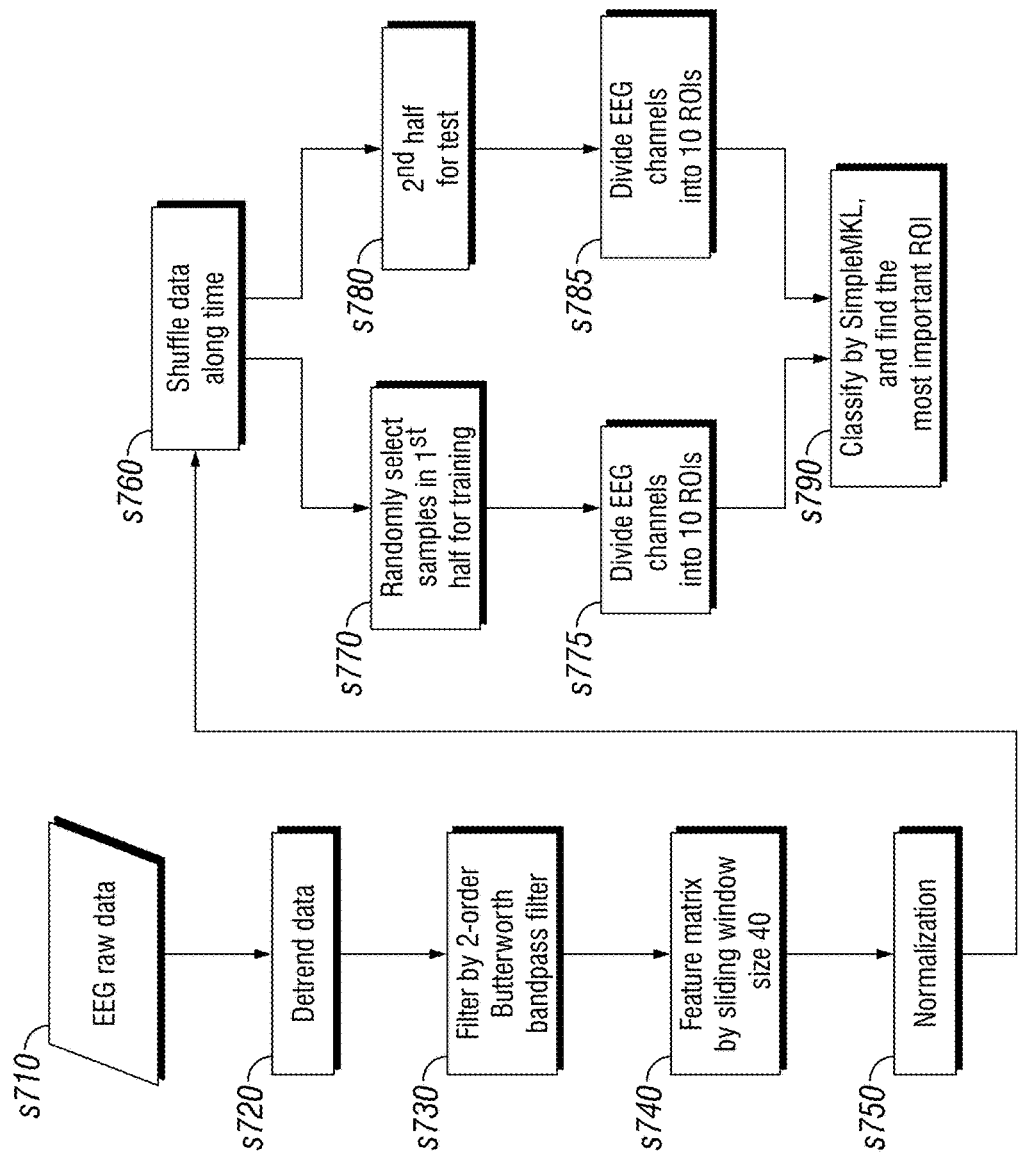
FIG. 7 shows a flow chart of an illustrative embodiment of a classification method for decoding.

FIG. 7 shows a flow chart of an illustrative embodiment of a classification method for decoding motor intent. In step s710, EEG raw data is received by the BMI. The data may be detrended in step s720. The data may then be filtered in step s730, such as by a 2-order Butterworth bandpass filter. A feature matrix may be created in step s740 (e.g. sliding window size 40). Next, the data may be normalized in step s750, and the process may proceed to shuffling data along time in step s760. In step s770, samples from the $1^{st}$ half may be randomly selected for training, and in step s775 EEG channels may be divided into regions of interests (ROIs). As a nonlimiting example, these training EEG channels may be divided into 10 ROIs. The $2^{nd}$ half of samples may be selected for testing in step s780, and in step s785 EEG channels may be divided into ROIs. As a nonlimiting example, testing EEG channels may be divided into 10 ROIs. The EEG channels from step s775 and s785 may be classified and the most important ROIs may be found in step s790. For example, classification may utilize simpleMKL, an algorithm for multiple kernel learning.

Figure 8:
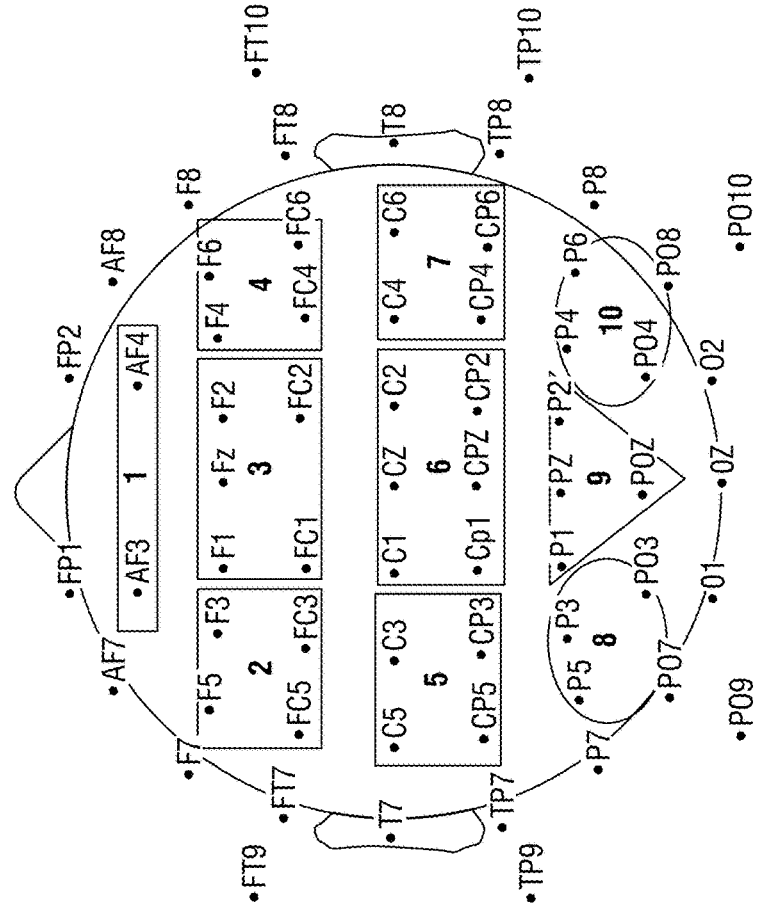
FIG. 8 is an illustrative example of regions of interest.

FIG. 8 is an illustrative example of regions of interests or ROIs. As a nonlimiting example, ROIs of a user's scalp may include anterior frontal (AF) 1, left frontal (LF) 2, middle frontal (MF) 3, right frontal (RF) 4, left fronto-central (LFC) 5, midline central (MC) 6, right fronto-central (RFC) 7, left centro-parietal (LCP), middle parietal (MP), and/or right centro-parietal (RCP).

Figure 10A:
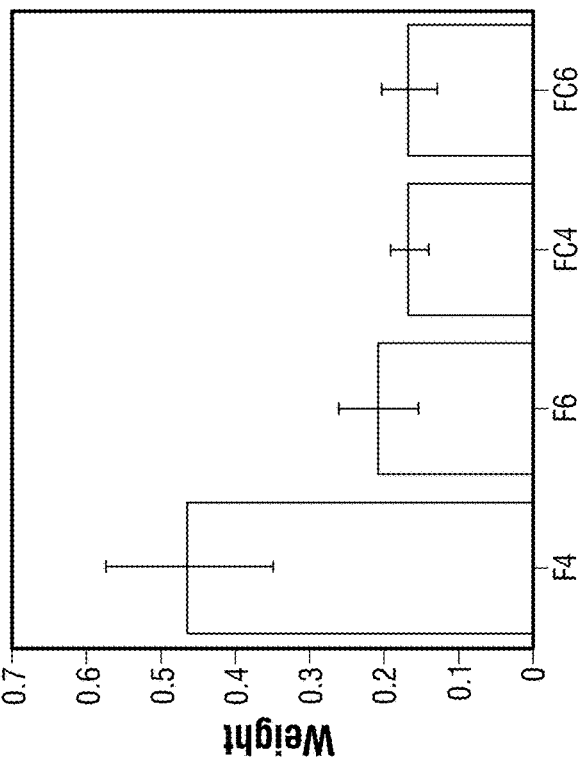
FIGS. 10a-10b show weight v. channel for Groups 3 and 4 respectively.
Figure 10B:
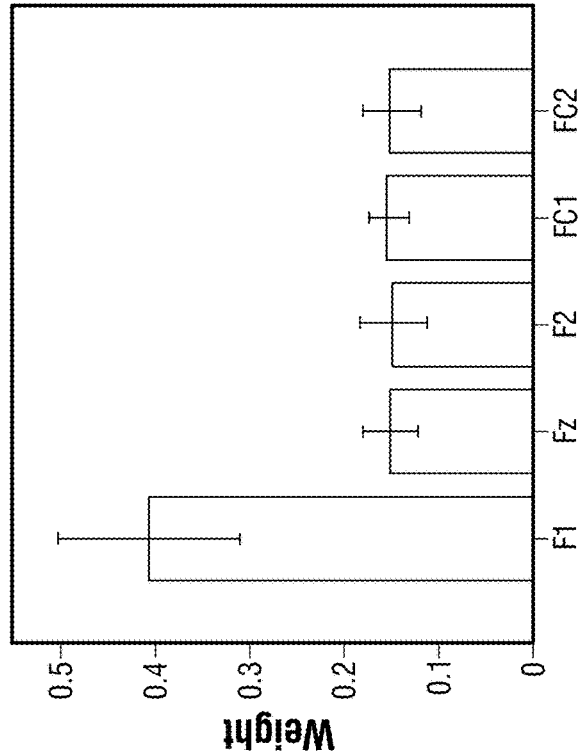

FIGS. 9a-9b show a comparison of able-bodied subjects and spinal cord injury (SCI) patients with 4-class data (standing, walking, turning left, and turning right) using BMI to Rex. The central regions (e.g. ROI 3, 4, 5, 6, may also include 2 and 7) get relative high weights learned from the multiple kernel learning (MKL) method. By comparing the above results, the most important group for the able-bodied subject is ROI 3, while for the SCI patient is ROI 4. FIGS. 10a-10b show the channels in group 3 and 4 to see which channel has the highest weight. As can be seen from the results, the most important channel is F1 for ROI and channel F4 for ROI 4. FIG. 11a shows a table of output (decoding) accuracy OA (%) and mean weight of group 4 for different sessions. Longitudinal 2-class [Standing, Walking] data from the SCI patient was obtained. FIGS. 11b-11C show plots of OA and the weight for ROI 4 as a function of session.

Figure 12:
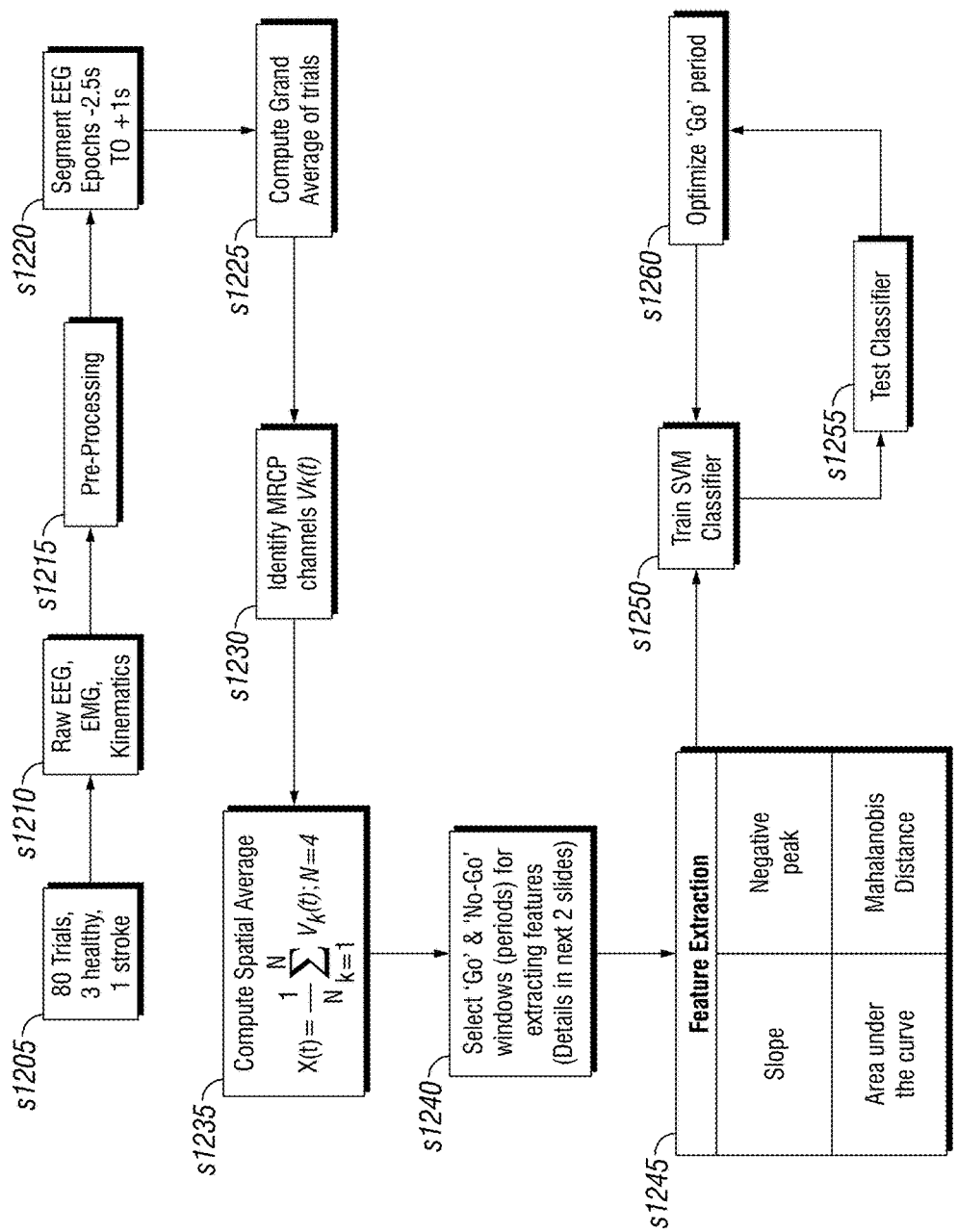
FIG. 12 shows an illustrative embodiment of a method for training an EEG classifier for detecting intent.

FIG. 12 is an illustrative embodiment of training an EEG classifier for detecting user intent. In step s1205, trials may be conducted to allow raw EEG, electromyography (EMG), and kinematics data to be obtained in step s1210. As a nonlimiting example, 80 trials with 3 healthy and 1 stroke user may be conducted. The raw EEG, electromyography (EMG), and kinematics data may be pre-processed in step s1215. Data may be segmented into EEG epochs in step s1220. As a nonlimiting example, data may be segmented into EEG Epochs of −2.5 s to +1 s. A grand average of trials may be computed in step s1225. In step s1230, movement-related cortical potentials (MRCP) channels $V_k(t)$ may be identified, and spatial averages may be computed in step s1235. 'Go' and 'No-Go' windows (periods) for extracting features may be selected in step s1240, which is discussed further in the next two figures. In step s1245, features are extracted (e.g. slope, negative peak, area under the curve, mahalanobis distance, or the like). An SVM classifier may be trained in step s1250, and the classifier may be tested in step s1255. The 'Go' period may be optimized in step s1260. As shown, steps s1250-s1260 may be repeated as necessary.

Figures 13A, 13B:
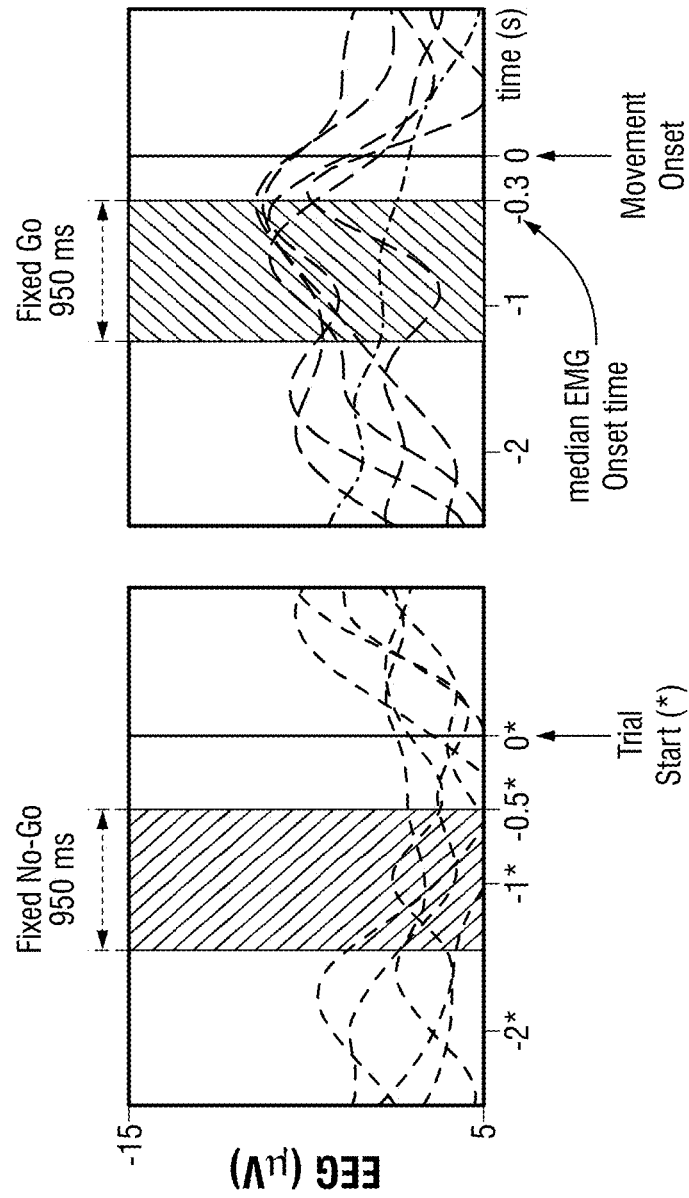
FIGS. 13a-13b show a 'fixed no-go' and 'fixed go' window approaches respectively.
Figures 14A, 14B:
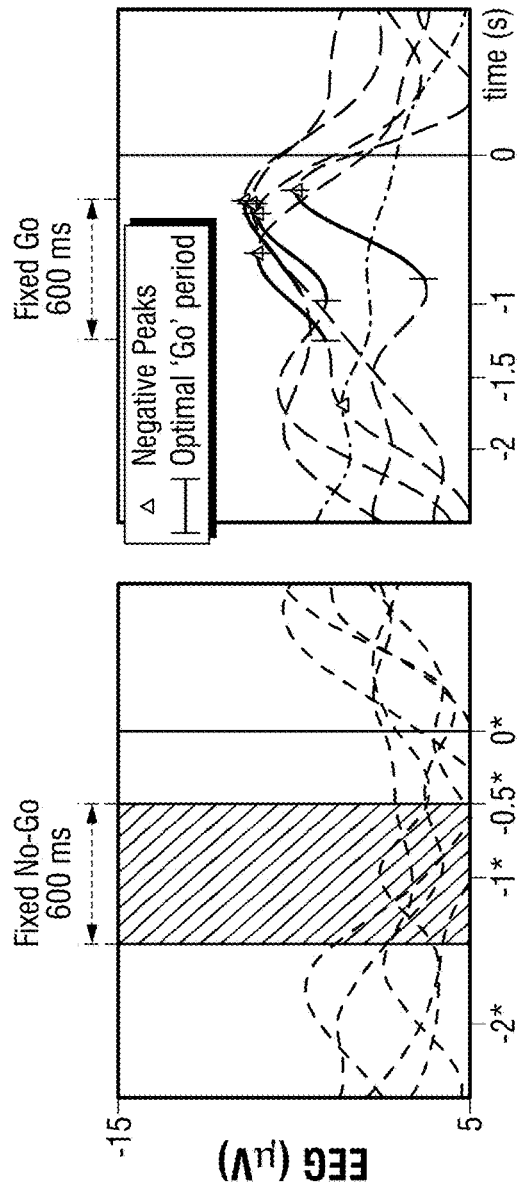
FIGS. 14a-14b show a 'fixed no-go' and 'flexible go' window approaches respectively.

FIGS. 13a-13b illustrate a 'Fixed No-Go' and 'Fixed Go' window approaches. As shown in FIG. 13a, 'Fixed No-Go' may involve selecting a window (or period) of EEG data a predetermined amount of time prior to the trial start. 'Fixed Go' may involve selecting a window of EEG data a predetermined amount of time prior to movement onset of the exoskeleton as shown in FIG. 13b. In some embodiments, this may be before the median EMG onset time. FIGS. 14a-14b illustrate a 'Flexible Go' window approach in comparison to a 'Fixed No-Go' approach. A 'Fixed No-Go' approach is shown in FIG. 14a. In a 'Flexible Go' window approach, negative peak values of spatially averaged MCRPs for each trial may be found, such as within [−2 to 0s]. Then the 'Go' window may be extracted by starting at the negative peak and traversing an optimized window into past. As a nonlimiting example, FIG. 14b shows traversal 600 ms (optimized) into the past. In some embodiments, trials for which the negative peak occurred too early with respect to the movement onset may be rejected during training of the classifier, such as negative peaks occurring earlier than 1.5s before movement onset. As shown, the optimal 'Go' period may vary from plot to plot, whereas 'Fixed No-Go' and 'Fixed Go' have set windows that are the same for each plot. The proposed 'flexible' (adaptive) Go/No-Go approach therefore optimizes the analysis window resulting in higher decoding accuracies than other methods.

Figure 15:
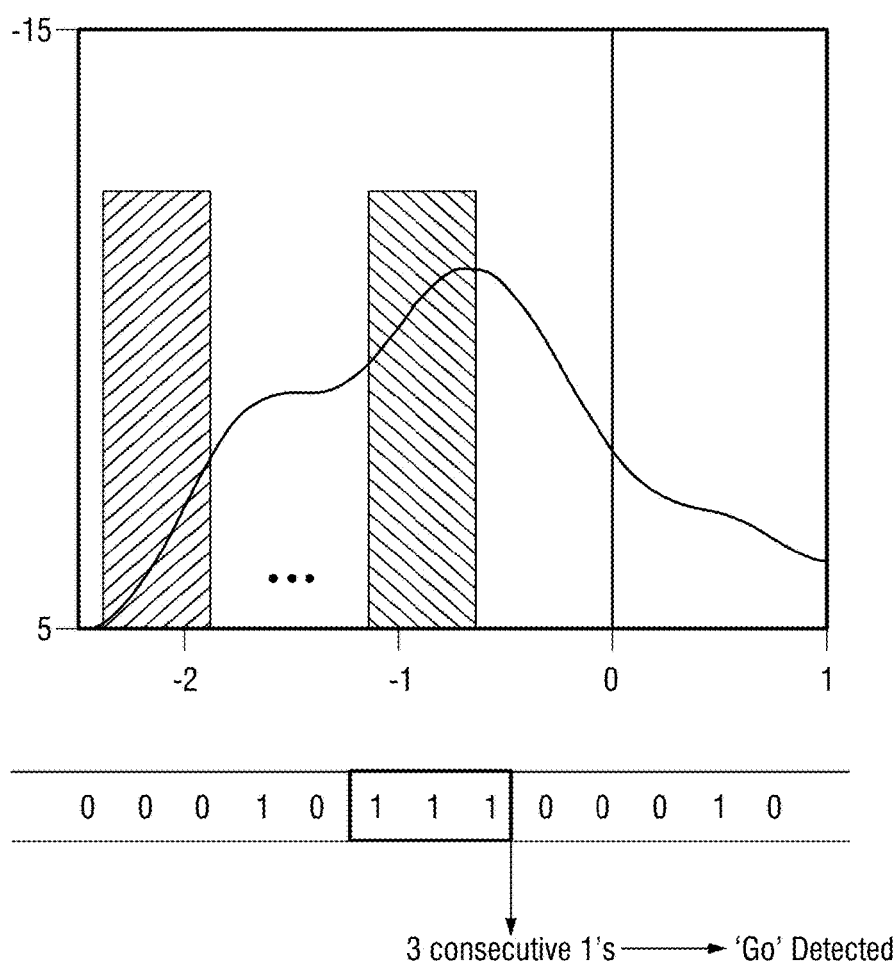
FIG. 15 shows a method for validating a classifier.

FIG. 15 shows a method for validating a classifier. Classifier performance may be evaluated utilizing sliding windows with an overlap. As a nonlimiting example, classifier's performance may be evaluated during online simulation of test trials using 600 ms (or 950 ms) sliding windows with 50 ms overlap. 'Go' incidents may be detect when a certain number of consecutive positives are detected. As a nonlimiting example, a 'Go' incident is detected when 3 consecutive 1's are detected.

Figure 16:
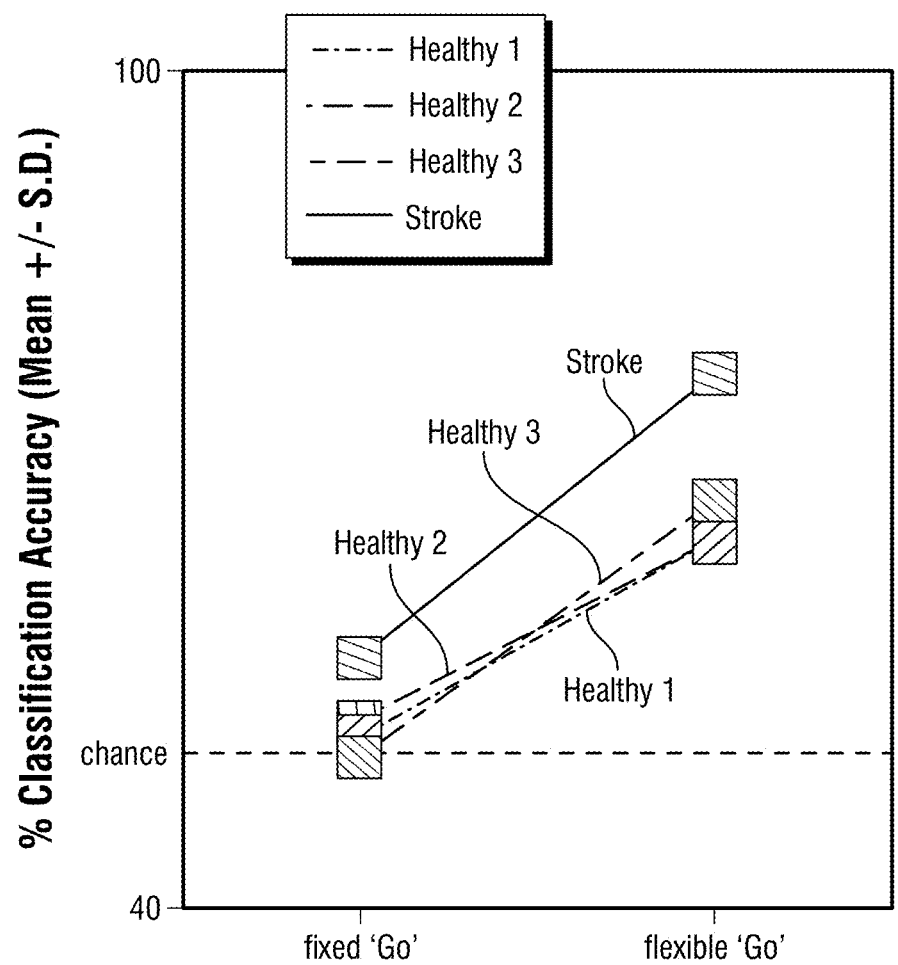
FIG. 16 shows classification accuracy results.
Figures 17A, 17B:
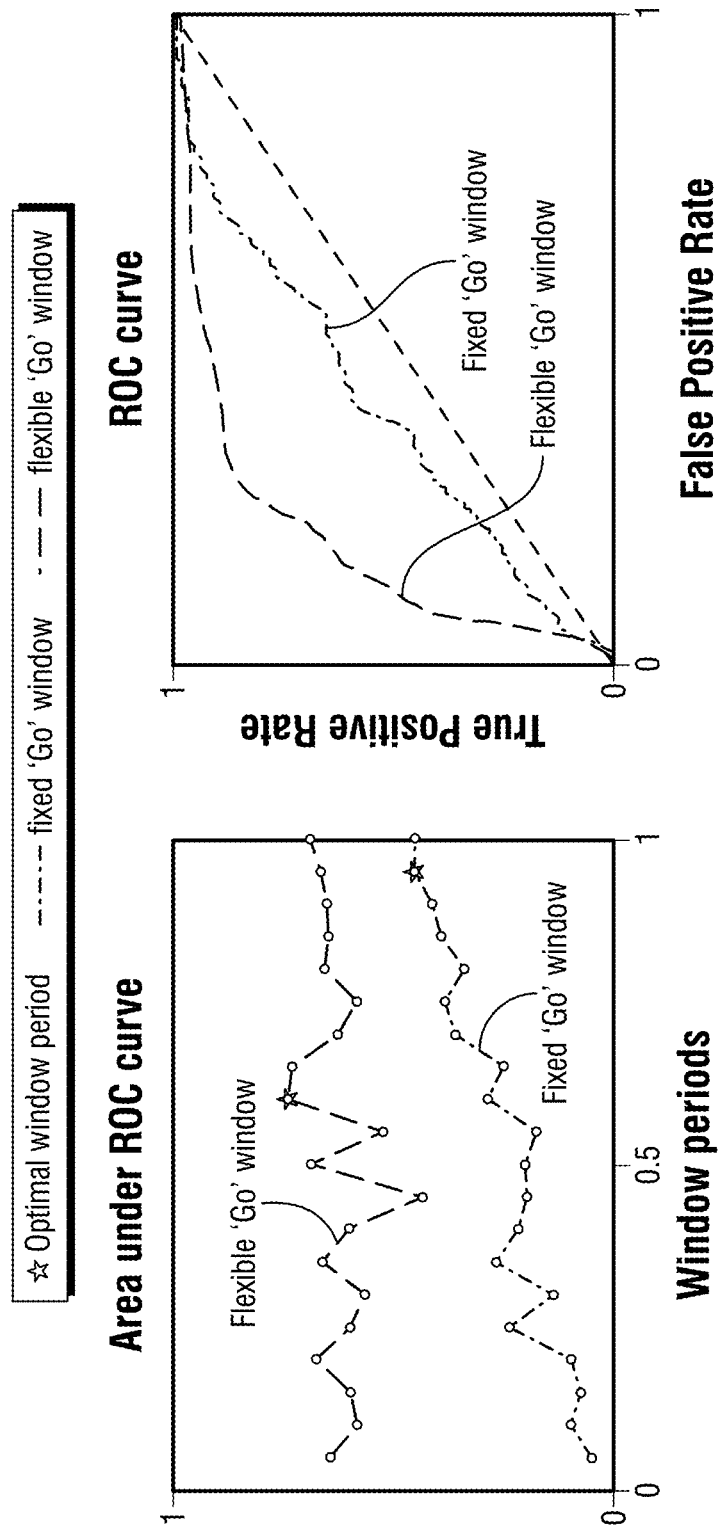
FIGS. 17a-17b respectively show area under the ROC curve and ROC curve graphs for optimization of a 'Go' period.
Figure 18:
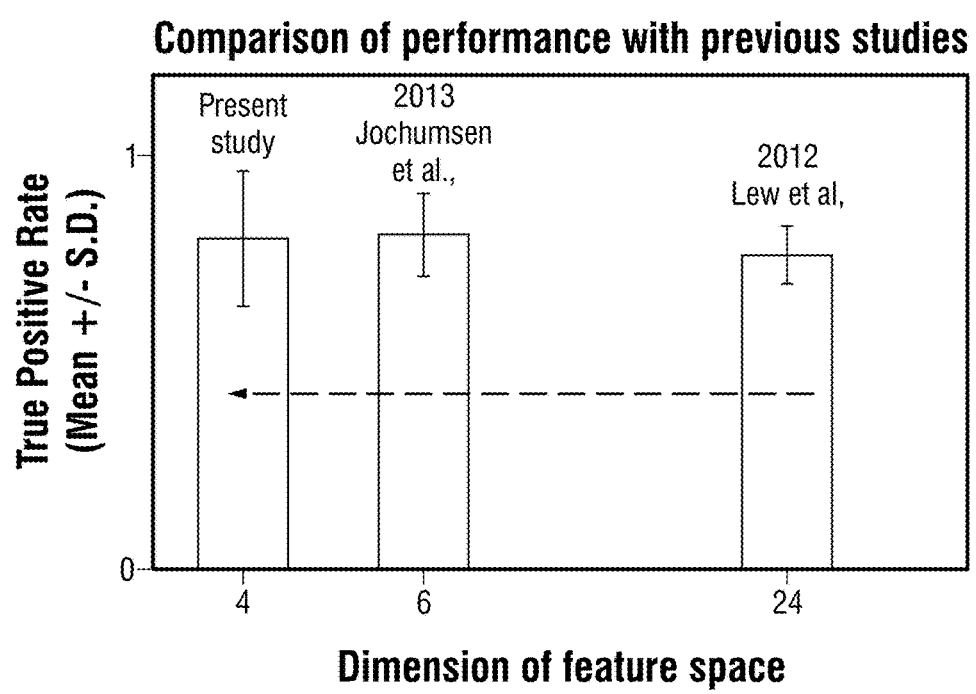
FIG. 18 shows accuracy results in comparison to other recent studies.

FIG. 16 shows classification accuracy results. Classification Accuracy=(Number of correctly predicted trials×100)/(Total number of trials). Classification accuracy percentage was calculated for fixed 'Go' and flexible 'Go' for the 3 healthy and 1 stroke user. FIGS. 17a-17b show optimization of a 'Go' period. To optimize period of fixed or flexible 'Go' windows, area under the (receiver operating characteristics) ROC curve was calculated for set periods. As a nonlimiting example, the set period may range from equal to or between 0.05s to 1s. The period with a maximum area is the optimal 'Go' period. FIG. 18 shows a comparison of performance with previous studies. As shown in figure below, the present study's accuracy closely matches with other similar studies in other literature. The present study's smaller dimension feature space will reduce the computational overheads during real-time closed-loop control.

In some embodiments, the present disclosure contemplates embedding the identification of the reduced dimension and knn parameters, as well as building the GMM distribution model in real-time. In an embodiment, the present disclosure also contemplates accounting for the inherent time delays associated with the exoskeleton to increase the responsiveness to the commanded motions. As discussed previously, the exoskeleton performs a series of motion-cycles before executing a new command. In several trials, the transmission of a new command before the execution of the previously received command was completed was observed. For example, before a stop command was fully executed, a new walk command would be received from the BMI system, which explains the difference between the observed and recorded command percentages over the entire data set. Nevertheless, an increase in accuracy was observed in both cases.

Embodiments described herein are included to demonstrate particular aspects of the present disclosure. It should be appreciated by those of skill in the art that the embodiments described herein merely represent exemplary embodiments of the disclosure. Those of ordinary skill in the art should, in light of the present disclosure, appreciate that many changes can be made in the specific embodiments described and still obtain a like or similar result without departing from the spirit and scope of the present disclosure. From the foregoing description, one of ordinary skill in the art can easily ascertain the essential characteristics of this disclosure, and without departing from the spirit and scope thereof, can make various changes and modifications to adapt the disclosure to various usages and conditions. The embodiments described hereinabove are meant to be illustrative only and should not be taken as limiting of the scope of the disclosure.

What is claimed is:

1. A method for decoding user intent from brain activity, the method comprising:
   obtaining brain activity data with an electroencephalography (EEG);
   transmitting the brain activity data from the EEG to a brain-machine interface (BMI); and
   using the BMI:
   arranging the brain activity data into a feature matrix, wherein the feature matrix provides a collection of feature vectors over time, and a feature vector represents an amplitude modulation of the brain activity data while a user conducts a specific type of motion with a robotic exoskeleton;
   calculating probabilities of a current feature vector from the collection feature vectors belonging to a class selected from a plurality of classes, wherein the selected class represents a desired movement or posture by a user;
   identifying a class label in accordance with the probabilities calculated, wherein the class label identified is associated with a maximum probability;
   utilizing dimensionality reduction to reduce dimensionality of the brain activity data in the feature matrix;
   identifying movement-related cortical potentials (MRCP) channels;
   finding negative peak values for a spatially averaged MRCP signal computed from the MRCP channels;
   extracting a 'Go' window starting at a negative peak of the spatially averaged MRCP signal occurring within a set period of time from voluntary movement onset, wherein the 'Go' window traverses into a past a predetermined amount of time from the negative peak;
   mapping states of the robotic exoskeleton to the feature matrix; and
   transmitting commands to the robotic exoskeleton, wherein the commands correspond to the mapped states.

2. The method of claim 1, further comprising filtering the brain activity data received by the BMI to obtain delta band brain activity data.

3. The method of claim 2, further comprising standardizing the delta band brain activity data.

4. The method of claim 1, wherein the dimensionality reduction is performed utilizing a Local Fisher's Discriminant Analysis (LFDA).

5. The method of claim 4, wherein the dimensionality reduction is performed in real-time.

6. The method of claim 1, wherein the mapping of the feature matrix is performed utilizing a Gaussian Mixture Model (GMM).

7. The method of claim 1, wherein a specified window size of the brain activity data is received by the BMI.

8. The method of claim 1, wherein separate channels of the brain activity data are used to create the feature matrix.

9. The method of claim 1, further comprising converting the class label identified into an associated motion of the robotic exoskeleton.

10. A neural interface system comprising:
    a robotic exoskeleton;
    an electroencephalography (EEG) for obtaining brain activity data;
    a brain-machine interface (BMI) coupled to the robotic exoskeleton and EEG, wherein the BMI arranges the brain activity data into a feature matrix, the feature matrix provides a collection of feature vectors over time, and a feature vector represents an amplitude modulation of the brain activity data while a user conducts a specific type of motion with the robotic exoskeleton,
    wherein further the BMI calculates probabilities of a current feature vector from the collection of feature vectors belonging to a class selected from a plurality of classes, wherein the selected class represents a desired movement or posture by a user, and the BMI identifies a class label in accordance with the probabilities calculated, wherein the class label identified is associated with a maximum probability, the BMI reduces dimensionality of the brain activity data in the feature matrix, and wherein
    wherein further the BMI identifies movement-related cortical potentials (MRCP) channels, finds negative peak values for a spatially averaged MRCP signal computed from the MRCP channels, extracts a 'Go' window starting at a negative peak of the spatially averaged MRCP signal occurring within a set period of time from voluntary movement onset, and the 'Go' window traverses into a past a predetermined amount of time from the negative peak, and
    the BMI maps states of a robotic exoskeleton to the feature matrix, and the BMI transmits commands corresponding to the mapped states to the robotic exoskeleton.

11. The system of claim 10, further comprising a filter for filtering the brain activity data received by the BMI to obtain delta band brain activity data.

12. The system of claim 11, wherein the BMI standardizes the delta band brain activity data.

13. The system of claim 10, wherein the dimensionality reduction is performed utilizing a Local Fisher's Discriminant Analysis (LFDA).

14. The system of claim 13, wherein the dimensionality reduction is performed in real-time.

15. The system of claim 10, wherein the feature matrix is mapped utilizing a Gaussian Mixture Model (GMM).

16. The system of claim 10, wherein a specified window size of the brain activity data is provided to the BMI from the EEG.

17. The system of claim 10, wherein separate channels of the brain activity data are used to create the feature matrix.

18. The system of claim 10, wherein the BMI converts the class label identified into an associated motion of the robotic exoskeleton.

* * * * *